(12) United States Patent
Stimson

(10) Patent No.: US 10,487,127 B2
(45) Date of Patent: *Nov. 26, 2019

(54) COMPOSITIONS AND METHODS RELATING TO THE TREATMENT OF DISEASES

(71) Applicant: ALFACYTE LTD, Newhouse (GB)

(72) Inventor: William Stimson, Edinburgh (GB)

(73) Assignee: ALFACYTE LTD, Newhouse (GB)

( * ) Notice: Subject to any disclaimer, the term of this patent is extended or adjusted under 35 U.S.C. 154(b) by 94 days.

This patent is subject to a terminal disclaimer.

(21) Appl. No.: 15/118,034

(22) PCT Filed: Mar. 12, 2015

(86) PCT No.: PCT/GB2015/050717
§ 371 (c)(1),
(2) Date: Aug. 10, 2016

(87) PCT Pub. No.: WO2015/136287
PCT Pub. Date: Sep. 17, 2015

(65) Prior Publication Data
US 2017/0174735 A1    Jun. 22, 2017

(30) Foreign Application Priority Data

Mar. 12, 2014    (GB) .................................. 1404403.6

(51) Int. Cl.
| | |
|---|---|
| A61K 38/21 | (2006.01) |
| A61K 39/35 | (2006.01) |
| A61K 39/39 | (2006.01) |
| A61K 39/00 | (2006.01) |
| C07K 14/56 | (2006.01) |

(52) U.S. Cl.
CPC .............. *C07K 14/56* (2013.01); *A61K 39/39* (2013.01); *A61K 2039/542* (2013.01); *A61K 2039/55522* (2013.01); *A61K 2039/57* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 6,350,589 B1 | 2/2002 | Morris et al. | |
| 9,522,173 B2* | 12/2016 | Stimson ............... | A61K 38/212 |
| 2006/0204473 A1 | 9/2006 | Blatt et al. | |

FOREIGN PATENT DOCUMENTS

| | | |
|---|---|---|
| WO | WO-9524212 A1 | 9/1995 |
| WO | WO-2005123112 A2 | 12/2005 |

OTHER PUBLICATIONS

Kolchanov, 1988, Journal of Molecular Evolution, vol. 27, pp. 154-162. (Year: 1988).*
Pasquo, 2012, PLoS ONE, vol. 7, Issue 2, e32555. (Year: 2012).*
Aricò, Eleonora, et al.; "Interferon-α as Antiviral and Antitumor Vaccine Adjuvants: Mechanisms of Action and Response Signature"; Journal of Interferon & Cytokine Research, vol. 32, No. 6; Jun. 2012; pp. 235-247.
Tilg, Herbert; "Viewpoints in Digestive Diseases: New Insights into the Mechanisms of Interferon Alfa: An Immunoregulatory and Anti-Inflammatory Cytokine"; Gastroenterology, vol. 112, No. 3; Mar. 1997; pp. 1017-1021.
Souillet, G., et al.; "Alpha-Interferon Treatment of Patient with Hyper $I_gE$ Syndrome"; The Lancet, vol. 333, No. 8651; Jun. 17, 1989; p. 1384.
Weisser, Dagmar, "International Search Report," as prepared for PCT/GB2015/050717, dated Sep. 17, 2015, seven pages.

* cited by examiner

*Primary Examiner* — Daniel E Kolker
*Assistant Examiner* — Jegatheesan Seharaseyon
(74) *Attorney, Agent, or Firm* — Winstead PC

(57) ABSTRACT

The present invention relates to compositions and methods for promoting the induction of a cell-mediated immune response (such as that mediated by Th1 cells) and the suppression of a humoral or allergic immune response (such as that mediated by Th2 and Th17 cells). In particular, the invention relates to compositions and methods for preventing or treating allergy, such as food allergy, and associated allergic diseases, and conditions where an exaggerated Th17 response plays a detrimental role. The invention further extends to the use of the compositions of the invention in the treatment and/or prophylaxis of allergy and associated allergic diseases and also of cancer.

7 Claims, 14 Drawing Sheets

Specification includes a Sequence Listing.

Figure 9.

CDLPQTHSLGNRRALILLGQMGRISPFSCLKDRHDFRIPQEEFD
GNQFQKAQAISVLHEM

MQQTFNLFSTENSSAAWEQTLLEKFSIELFQQMNDLEACVIQEV
GVEETPLMNEDSILAV

RKYFQRITLYLIERKYSPCAWEVVRAEIMRSLSFSTNLQKRLRRK
D
(SEQ ID NO: 1)

Figure 10.

Reverse translation of amino acid sequence SEQ ID NO: 1 providing most likely codons.

```
tgcgatctgccgcagacccatagcctgggcaaccgccgcgcgctgattctgctgggccag
atgggccgcattagcccgtttagctgcctgaaagatcgccatgatttcgcattccgcag
gaagaatttgatggcaaccagtttcagaaagcgcaggcgattagcgtgctgcatgaaatg
atgcagcagacctttaacctgtttagcaccgaaaacagcagcgcggcgtgggaacagacc
ctgctggaaaaatttagcattgaactgtttcagcagatgaacgatctggaagcgtgcgtg
attcaggaagtgggcgtggaagaaaccccgctgatgaacgaagatagcattctggcggtg
cgcaaatattttcagcgcattaccctgtatctgattgaacgcaaatatagcccgtgcgcg
tgggaagtggtgcgcgcggaaattatgcgcagcctgagctttagcaccaacctgcagaaa
cgcctgcgccgcaaagat    (SEQ ID NO: 2)
```

Figure 11.

Reverse translation of amino acid sequence SEQ ID NO: 1 providing consensus codons.

```
tgygayytnccncaracncaywsnytnggnaaymgnmgngcnytnathytnytnggncar
atgggnmgnathwsnccnttywsntgyytnaargaymgncaygayttymgnathccncar
gargarttygayggnaaycarttycaraargcncargcnathwsngtnytncaygaratg
atgcarcaracnttyaayytnttywsnacngaraaywsnwsngcngctgggarcaracn
ytnytngaraarttywsnathgarytnttycarcaratgaaygayytngargcntgygtn
athcargargtnggngtngargaraacccnytnatgaaygargaywsnathytngcngtn
mgnaartayttycarmgnathacnytntayytnathgarmgnaartaywsnccntgygcn
tgggargtngtnmgngcngarathatgmgnwsnytnwsnttywsnacnaayytncaraar
mgnytnmgnmgnaargay  (SEQ ID NO: 3)
```

COMPOSITIONS AND METHODS RELATING TO THE TREATMENT OF DISEASES

FIELD OF THE INVENTION

The present invention relates to compositions and methods for promoting the induction of a cell-mediated immune response (such as that mediated by Th1 cells) and the suppression of a humoral or allergic immune response (such as that mediated by Th2 and Th17 cells). In particular, the invention relates to compositions and methods for preventing or treating allergy, such as food allergy, and associated allergic diseases, and conditions where an exaggerated Th17 response plays a detrimental role. The invention further extends to the use of the compositions of the invention in the treatment and/or prophylaxis of allergy and associated allergic diseases and also of cancer.

BACKGROUND TO THE INVENTION

Cytokines are immunomodulatory proteins that mediate immune system activation and responses, such as cell-mediated immunity and allergic type humoral responses. T lymphocytes (T cells), which are a major source of cytokines, possess antigen-specific receptors (the T cell receptor) on their cell surface, which allows recognition of foreign antigens. There are two main subsets of T lymphocytes, these being distinguished by the presence of cell surface markers known as CD4 and CD8. T lymphocytes expressing CD4 are also known as helper T cells, and these are regarded as being the most prolific cytokine producers. This subset can be further subdivided into Th1 cells and Th2/T17 cells, and the cytokines they produce are known as Th1-type cytokines and Th2/Th17-type cytokines respectively.

Th1 cells are characterized by the production of pro-inflammatory cytokines such as IFN-γ, IL-2, and TNF-β. Th1 cells are involved in cell-mediated immunity (CMI), this being the immune response typically mounted against viruses and intracellular pathogens. The cell-mediated response also eliminates cancerous cells and stimulates delayed-type hypersensitivity (DTH) skin reactions.

Th2 cells are characterized by the production of Interleukin-4 (IL-4), Interleukin-5 (IL-5), Interleukin-9 (IL-9), Interleukin-10 (IL-10) and Interleukin-13 (IL-13). Th2 cells are thought to play a role in allergy responses. Cytokines such as IL-4 generally stimulate the production of antibodies (the so called "humoral immune response") directed towards extracellular organisms, such as parasites. IL-5 stimulates eosinophil responses, also part of the immune response toward large extracellular parasites.

Th17 cells secrete IL-17 and are involved in immune regulation in cancer and allergic reactions. Functionally, Th17 cells play a role in host defence against extracellular pathogens by mediating the recruitment of neutrophils and macrophages to infected tissues. They are, therefore, largely part of the humoral response together with Th2 cells. Identification of the Th17 family of effector T cells represented a major recent breakthrough. The IL-17 cytokine family is a group of cytokines including IL-17A, B, C, D, IL-17E (IL-25) and IL-17F. It is increasingly recognized that besides T cells, other cells such as NK cells and neutrophils might also be an important source of IL-17. Besides IL-17A, the major cytokine produced by Th17 cells, these cells also release IL-17F, IL-21 and IL-22.

It is hypothesised that in certain circumstances, the Th1 response or the Th2/Th17 response can cause disease. An over-reactive Th1 response can generate organ-specific autoimmune disease such as arthritis, multiple sclerosis, or Type I diabetes, while an over-reactive Th2/Th17 response may underlie allergy and atrophy. It is currently believed that Th17 cells play a major role in host defence against pathogens and an exaggerated Th17 response may lead to severe inflammatory responses and autoimmune diseases—inflammatory bowel diseases (IBD), namely, ulcerative colitis (UC) and Crohn's disease (CD), are chronic inflammatory processes of the gastrointestinal tract. In these diseases a disturbed and exaggerated immune response, mainly towards the endogenous microflora, plays a major role. IL-17 expression is increased in both UC and CD. Type I IFNs have been studied in clinical trials in patients with UC and demonstrated efficacy in selected studies. As anti-viral cytokines, it is now known that Type I IFNs can regulate the development of Th17 cells.

Either a Th1 response or a Th2/Th17 response can down-regulate the other and this is the basis for the so-called "Th1/Th2" hypothesis whereby an immune response may be skewed down either the Th1 or Th2/Th17 route, this being driven by the cytokine profile secreted by one cell group which may promote expansion of that cell type and restrict expansion of the opposing cell type.

Interferons (IFNs) are a family of proteins which are pleiotropic effectors of the immune system. Interferons may be classified into three distinct types—Type I interferons, Type II interferons and Type III interferons. Type I IFNs represent a family of highly homologous cytokines that have been found to activate a range of physiological responses, including anti-viral and anti-proliferative activities as well as playing an important role as activator of the immune response.

Type I interferons consist of interferon alpha (IFN-α), interferon beta (IFN-β), interferon kappa (IFN-κ), interferon tau (IFN-τ), interferon nu (IFN-ν) and interferon omega (IFN-ω)). IFN-α is represented in the genome by 13 genes (12 subtypes), some of which have allelic variants and the different IFN-α gene products are called subtypes. All interferon subtypes consist of 166 amino acids stabilised by two disulfide bonds, except for IFN-α2 which has one amino acid less. The homology to mouse IFN-α is 40%.

There are 2 forms of IFN-α: (i) recombinant IFN-alphas which are designated IFN-α2a and IFN-α2b, with only one amino acid difference (IFN-α2a was cloned from a tumour cell line and occurs as a polymorphic variant in human populations); and (ii) a multi-subtype IFN-α, sometimes called natural IFN-alpha, which is expressed from the leukocyte fraction of human blood challenged with Sendai virus or produced by cell lines e.g. lymphoblastoid. This product is highly purified with a final immunoaffinity step and contains six major subtypes, namely, IFN-α1, IFN-α2, IFN-α8, IFN-α10, IFN-α14, and IFN-α21, the first two being the major components.

It is known that different pathogens induce different IFN-α subtypes in vitro and that IFN-α subtypes have different antiviral activities. Infection via a variety of routes, including orally, has been shown to induce different subtype profiles. IFN-α subtypes bind to the same receptor, activate common signaling pathways and are expected to have the same biological functions. Similar to many cytokines, two of the natural IFN-α subtypes are glycosylated. IFN-α14 has N-linked glycosylation, while IFN-α2 has O-linked glycosylation. Glycosylation influences the structure and the polarisation of the molecule, but no effects have been demonstrated on receptor binding or direct physiological function. Nevertheless, glycosylation could modulate recognition by the immune system or increase the half-life in the circulation.

All IFN-α subtypes have anti-viral activities, by definition, although their absolute efficacy in this context may vary considerably. In addition, many other biological properties have been described, but with varying potencies, including immunomodulatory and anti-proliferative activities. The pleiotropic effects appear to be due to differential interaction with the receptor chains and signaling through different intracellular pathways to an array of effector molecules.

Overall, IFN-α is part of innate immunity with strong links into adaptive immunity. Both T and B-cells are activated. IFN-α promotes the induction of a Th1 immune response, one mechanism being possibly through the enhancement of IFN-α-inducible protein-10 (IP-10) expression in dendritic cells. Few studies deal with the role of subtypes in T helper-regulation while the cytolytic activity of both T-cells and NK-cells is enhanced.

IFN-α may have a key role in the regulation of the Th1 response. It has been shown that IFN-α treatment promotes Th1 cell differentiation indirectly (largely via IFN-γ), but also appears to suppress Th2 cell development through the suppression of IL-4 and IL-13 gene expression. IFN-α therefore is able to re-establish a Th1/Th2 population balance in diseases and infections that promote a Th2 cell imbalance. In recent years, it became evident that besides its anti-viral effects, several immunomodulatory functions are exerted by IFN-α. IFN-α can impact on dendritic cell differentiation and controls the expression of various pro-inflammatory cytokines such as IL-8 or IL-18 and induces several anti-inflammatory mediators such as IL-1 receptor antagonist (IL-1Ra), soluble TNF receptor p55, IL-10 and IL-18 binding protein. However, the mechanisms of actions of IFN-α are still only partly understood.

In patients with allergy or allergic disease, a Th2-predominant immune response is generated. Th2 cells secrete IL-4 and IL-13 driving B cells to produce Immunoglobulin E (IgE) antibodies specific to an allergen. An allergen is an antigen capable of stimulating a type-I hypersensitivity reaction in atopic individuals mainly through Immunoglobulin E (IgE)-mediated responses. Following that, IgE binds to its high affinity receptor on mast cells, skin cells and mucosal tissues. Upon exposure to the allergen, mast cells release their contents, which include histamine, leukotrienes and prostaglandins. This causes allergic symptoms including, but not limited to, red eyes, itchiness, runny nose, eczema, urticaria, angioedema, shortness of breath, wheezing, coughing, an asthma attack, abdominal pain, vomiting, diarrhoea or even anaphylaxis.

Allergic diseases are among the most common form of chronic illness. The World Health Organisation estimates that over 20 percent of the world population is affected and Europe alone has over 80 million sufferers (Global Allergy and Asthma European Network, 2008). An allergic reaction is usually caused by hypersensitivity of the immune system to an allergen, causing a misdirected immune response. Mild allergies, such as hay fever, are very common in the human population. Severe allergies can be caused by dietary allergens, such as food, by environmental allergens, such as the venom of stinging insects, by medication or can be genetically determined.

Food allergy is a major health concern, which is estimated to affect around 6% of young children and 3-4% of adults in Western societies. Food allergy is hypothesised to result from a breakdown in oral tolerance to ingested antigens or allergens. Food allergies and associated allergic diseases include, but are not limited to, dairy (milk) allergy, including Heiner syndrome, egg allergy, soya allergy, fish (shellfish) allergy, peanut and tree nut allergy, sesame and other seed allergy, gluten (wheat) and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

Management and treatment of allergic disease is usually via three general approaches: (i) avoidance of the allergen; (ii) medications that target disease symptoms and (iii) conventional immunotherapy, known as desensitisation, which aims to enhance the Th1 response in established disease. However, these approaches are far from ideal. Avoidance of allergens is not always possible, medications that target disease symptoms, such as anti-histamines, provide only short-term relief and desensitisation involves the use of the actual allergen, which can result in potentially frequent harmful side-effects. The possibility of anaphylaxis is never completely eliminated in patients suffering from allergic diseases and this causes a great deal of stress to the patient and their families.

The present inventor submits that it would be desirable to develop an immunotherapeutic approach which involves safer use of an allergen, as lower doses may be employed, and provides longer-term protection against the allergic reaction. Since allergy results from over-reactivity of Th2/Th17 cells and a corresponding lack of activity of the Th1 response, a medication that is able to modify and balance a misdirected Th2/Th17 response would be beneficial in preventing the allergic reaction. Such a medication would further be suitable to treat diseases and conditions where an exaggerated Th17 response plays a role, such as IBD. Additionally, the inventors consider the ability to enhance of a Th1-mediated immune response and suppress a Th2/Th17-mediated immune response would be useful in the provision of compositions that mediate immune response in subjects with cancer.

SUMMARY OF THE INVENTION

Following extensive experimentation, the present inventor has made the surprising discovery that the administration of a specific interferon alpha (IFN-α) subtype selected from IFN-α10, IFN-α14, a hybrid thereof preferably wherein the hybrid includes the primary interferon receptor binding sites of IFN-α10 and IFN-α14 or mixtures of at least two of IFN-α10, IFN-α14, or a hybrid thereof as part of a composition to modulate the immune system, such as a vaccine, for example comprising an allergen, can result in enhanced activation of the Th1 immune response and suppression of the Th2/Th17 immune response. This has led to the identification by the inventor of improved therapeutic compositions which have utility in the treatment and/or prophylaxis of allergy and allergic diseases and diseases and conditions where an exaggerated Th17 response plays a role and also to cancer. In particular, the inventor has identified that the administration of at least one food allergen which is capable of mediating a Th2/Th17 immune response with IFN-α10, IFN-α14 or a hybrid thereof preferably wherein the hybrid includes the primary interferon receptor binding sites of IFN-α10 and IFN-α14 can be used in the treatment of food allergy and associated allergic diseases.

Moreover, the inventor has identified that the administration of a tumour antigen, either a tumour associated or a tumour specific antigen, in combination with a specific interferon alpha (IFN-α) subtype selected from IFN-α10, or IFN-α14, or a hybrid thereof, preferably wherein the hybrid includes the primary interferon receptor binding sites of IFN-α10 and IFN-α14 or mixtures of at least two of IFN-α10, IFN-α14, or a hybrid thereof as part of a composition to modulate the immune system, such as a vaccine, can be used in the treatment of cancer. Suitably, the cancer may be hepatic cancer, lung cancer, in particular non-small cell lung cancer, ovarian cancer, breast cancer, skin cancer, melanoma or genitourinary cancer. Suitably, the tumour associated antigen may be selected from a prostate tumour, a renal cell tumour and a bladder tumour.

Accordingly a first aspect of the present invention, provides a method for the treatment and/or prophylaxis of a condition where an enhancement of a Th1-mediated immune response and suppression of a Th2/Th17-mediated immune response are desired, said method comprising the step of:

(i) administering to a subject in need thereof a therapeutically effective amount of at least one interferon alpha subtype selected from IFN-α10, IFN-α14 and a hybrid thereof wherein the hybrid includes the primary interferon receptor binding sites of IFN-α10 and IFN-α14.

In embodiments a subject in need thereof may be administered a mixture of at least two of IFN-α10, IFN-α14, or a hybrid thereof.

Whilst not wishing to be bound by theory, the inventor believes that proteins comprising the amino acid sequence of IFN-α10 have greater affinity to interferon receptor 2 and proteins comprising the amino acid sequence of IFN-α14 have greater affinity to interferon receptor 1. Thus, substitution of a protein comprising an IFN-α10 amino acid sequence with amino acids of IFN-α14 which allow binding to interferon receptor 1 or substitution of a protein comprising an IFN-α14 amino acid sequence with amino acids of IFN-α10 which allow binding to interferon receptor 2 is considered to provide a IFN-α10 IFN-α14 hybrid protein which should have stronger binding affinity to both interferon receptors 1 and 2 than IFN-α10 or IFN-α14 alone. By including the primary interferon receptor binding sites of IFN-α10 and IFN-α14 is meant that the hybrid comprises amino acids selected from IFN-α10 and substituted into an IFN-α14 amino acid sequence to improve the ability of an IFN-α14 subtype to bind to an interferon receptor 2 and/or that the hybrid comprises amino acids selected from IFN-α14 and substituted into an IFN-α10 amino acid sequence to improve the ability of an IFN-α10 subtype to bind to an interferon receptor 1.

Suitably, several amino acid substitutions of protein comprising an IFN-α10 amino acid sequence with amino acids of IFN-α14 determined to be involved in binding to interferon receptor 1 may enhance the binding of the protein to interferon receptor 1. Suitably, an amino acid substitution of protein comprising an IFN-α14 amino acid sequence with amino acids of IFN-α10 determined to be involved in binding to interferon receptor 2 may enhance the binding of the protein to interferon receptor 2.

In embodiments the IFN-α10 IFN-α14 hybrid can substantially have the amino-acid sequence of IFN-α10, but be modified in a region between amino residues 80 to 120, suitably amino acid residues 92 to 115 or suitably between amino acid residues 90 to 110 or suitably between amino acid residues 84 to 104, (utilizing the numbering of the IFN-α10 sequence providing in FIG. 16) to provide the amino acids provided by the IFN-α14 sequence. It is considered the amino acid residues in these regions or parts of these regions provide for the binding of IFN-α14 to interferon receptor 1. In particular, the hybrid sequence may include at least one, at least two, at least three, at least 4, at least 5, or 6 modifications of the IFN-α10 sequence to provide the corresponding residues of the IFN-α14 sequence (suitably substituted residues are noted in bold in FIG. 9) or a conserved mutation thereof. In embodiments, six modifications are provided as indicated by the amino acids noted in bold in FIG. 9. In alternative embodiments, IFN-α14 can be utilised as a backbone structure of the hybrid and the residues which differ between the IFN-α10, IFN-α14 sequences at the N and C terminal regions of the sequences can be provided in the hybrid sequence as those present in the IFN-α10 sequence. Suitably at least 1, at least 2, at least 3, at least 4, at least 5, at least 6 or 7 substitutions of the IFN-α14 N-terminal sequence may be made to provide the hybrid sequence to provide residues from IFN-α10 at those amino acid positions wherein the amino acids are not shared/common between IFN-α10 and IFN-α14. Suitably, at least 1, at least 2, or 3 substitutions are provided at the IFN-α14 C terminal sequence to provide residues from IFN-α10 to the hybrid sequence at those amino acid positions which are not shared/common between IFN-α10 and IFN-α14. In embodiments at least 1, at least 2, at least 3, at least 4, at least 5, at least 6 or 7 substitutions from the N-terminal sequence and at least 1, at least 2, or 3 substitutions from the C-terminal sequence of the IFN-α14 are made to provide residues from IFN-α10 to the hybrid at those amino acid positions which have amino acids that are not shared/common between IFN-α10 and IFN-α14.

In embodiments, the hybrid comprises or consists of an amino acid sequence SEQ ID NO: 1 or a functionally active fragment or variant thereof.

In certain embodiments, the method includes a step of administering to the subject a therapeutically effective amount of a vaccine composition for treatment or prophylaxis of the condition where an enhancement of a Th1-mediated immune response and suppression of a Th2/Th17-mediated immune response are desired. The vaccine composition may be administered sequentially, separately or simultaneously with the at least one interferon alpha subtype.

By functionally active is meant an IL-α10 IL-α14 hybrid peptide comprising the primary interferon binding sites of IFN-α10 and IFN-α14 wherein the administration of peptide to a subject or expression of peptide in a subject promotes enhancement of Th1 medicated immune response and suppression of a Th2/Th17 mediated immune response. Further, functional activity may be indicated by the ability of a hybrid peptide to enhance a Th1 mediated immune response and to suppress a Th2/Th17 mediated response.

A fragment can comprise at least 50, preferably 100 and more preferably 150 or greater contiguous amino acids from SEQ ID NO: 1 and which is functionally active. Suitably, a fragment may be determined using, for example, C-terminal serial deletion of cDNA such as SEQ ID NO: 2 or SEQ ID NO: 3. Said deletion constructs may then be cloned into suitable plasmids. The activity of these deletion mutants may then be tested for biological activity as described herein.

By variant is meant an amino acid sequence which is at least 70% homologous to SEQ ID NO: 1, more preferably at least 80% homologous to SEQ ID NO: 1, more preferably at least 90% homologous to SEQ ID NO: 1, even more preferably at least 95% homologous to SEQ ID NO: 1, even more preferably at least 96% homologous to SEQ ID NO: 1, even more preferably at least 97% homologous to SEQ ID NO: 1 and most preferably at least 98% homology with SEQ ID NO: 1. A variant encompasses a polypeptide sequence of SEQ ID NO: 1 which includes substitution of amino acids, especially a substitution(s) which is/are known for having a high probability of not leading to any significant modification of the biological activity or configuration, or folding, of the protein. These substitutions, typically known as conserved substitutions, are known in the art. For example the group of arginine, lysine and histidine are known interchangeable basic amino acids. Suitably, in embodiments amino acids of the same charge, size or hydrophobicity may be substituted with each other. Suitably, any substitution may be selected based on analysis of amino acid sequence alignments of interferon alpha subtypes to provide amino acid substitutions to amino acids which are present in other alpha subtypes at similar or identical positions when the sequences are aligned. Hybrids, and variants and fragments thereof may be generated using suitable molecular biology methods as known in the art.

In certain embodiments, the vaccine composition comprises at least one antigen. In certain embodiments, the vaccine composition comprises at least one allergen capable of mediating a Th2/Th17 immune response, for example, a food allergen.

In aspects and embodiments of the invention the antigen can be a tumour antigen, for example a tumour specific antigen or a tumour associated antigen, in particular a tumour antigen can be of a hepatic carcinoma, lung cancer, in particular non-small cell lung cancer, ovarian cancer, breast cancer, skin cancer, melanoma or of a genitourinary cancer. In particular an antigen of a genitourinary cancer can include an antigen from a prostate cancer, renal cell carcinoma, or bladder cancer. Suitably, an antigen may be a tumour specific antigen or tumour associated antigen provided in an existing cancer vaccine in use or development which would benefit from an adjuvant that enhances T-cell immunity, in particular that enhances a Th1 response or provides an enhancement of a Th1 mediated immune response and suppression of a Th2/Th17-mediated immune response. Suitably a tumour specific or tumour-associated antigen may be obtained from a tumour of a subject to be treated. In embodiments only a tumour-associated antigen can be used.

In embodiments a tumour antigen, in particular an associated antigen may be an antigen for a prostate cancer antigen, in particular prostate-specific antigen. Suitably a method of providing a prostate specific antigen or a prostate cancer antigen with the interferon-alpha subtypes of the invention maybe used to treat prostate cancer, specifically castration-resistant prostate cancer.

As will be appreciated by a physician, the subjects who will benefit most from such treatments may be those with minimal disease, as there may be less chance of increasing tumour suppression of the immune system, additionally or alternatively such treatments may benefit subjects with advanced disease who may have significant tumour immune suppression and may benefit more from the use of vaccines in combination with other forms of treatment. Suitably the use of vaccines including tumour antigens, in particular tumour associated antigen may be in combination with other forms of immunotherapy, for example Sunitinib (Sutent by Pfizer) a tyrosine kinase inhibitor.

In embodiments specific tumour antigens, in particular tumour-associated antigens may be selected from the antigens utilised in the prostate cancer vaccines TroVax and Prostvac.

In embodiments a tumour antigen, in particular a tumour-associated antigen can be selected from renal cell carcinoma. Suitably a tumour antigen, for example a tumour-associated antigen for renal cell carcinoma may be selected from a heat shock protein or proteins of renal tumour cell lysates, in particular the antigen used in the potential vaccine MVA-5T4.

Suitably a tumour antigen may be MUC1 from melanoma.

In embodiments, a tumour antigen, for example a tumour-associated antigen can be selected from bladder cancer. Suitably a tumour-associated antigen may be selected from Bacille Calmette-Guerin (BCG) vaccine, human leukocyte antigen—A*2402 restricted epitope peptides, immucin peptide (a 21mer synthetic vaccine composed of the entire signal peptide of the MUC1 protein) human chorionic gonadotropin-colony stimulating factor, or human chorionic gonadotropin-beta.

In certain embodiments, the method therefore includes a step of administering to the subject a therapeutically effective amount of at least one allergen capable of mediating a Th2/Th17 immune response, for example, a food allergen or tumour antigen, for example a tumour associated antigen. The allergen maybe administered sequentially, separately or simultaneously with the at least one interferon alpha subtype.

Typically, the subject is a mammal, in particular a human. In certain embodiments, the subject can be suffering from a condition where an enhancement of a Th1-mediated immune response and suppression of a Th2/Th17-mediated immune response are desired.

According to a second aspect of the present invention, there is provided at least one interferon alpha subtype selected from IFN-α10, IFN-α14 and a hybrid thereof wherein the hybrid comprises the primary interferon binding sites of IFN-α10 and IFN-α14, in particular SEQ ID NO: 1 or a fragment or variant thereof for use in the treatment and/or prophylaxis of a condition where an enhancement of a Th1-mediated immune response and suppression of a Th2/Th17-mediated immune response are desired.

In embodiments there is provided a mixture of at least two of IFN-α10, IFN-α14, or a hybrid thereof.

In certain embodiments, the at least one interferon alpha subtype, in particular a hybrid IFN-α10 and IFN-α14 subtype, for example SEQ ID NO: 1, as described herein is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen, or a tumour antigen, in particular a tumour-associated antigen.

According to a third aspect of the present invention, there is provided use of at least one interferon alpha subtype selected from IFN-α10, IFN-α14 and a hybrid thereof wherein the hybrid comprises the primary interferon binding sites of IFN-α10 and IFN-α14, in particular wherein the hybrid can be SEQ ID No: 1 or a variant or fragment thereof in the preparation of a medicament for the treatment and/or prophylaxis of a condition where an enhancement of a Th1-mediated immune response and suppression of a Th2/Th17-mediated immune response are desired.

In embodiments there is provided a mixture of at least two of IFN-α10, IFN-α14, or a hybrid thereof.

In certain embodiments, the at least one interferon alpha subtype is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen, or a tumour antigen, in particular a tumour associated antigen.

According to a further aspect of the present invention, there is provided a composition comprising:
(i) a vaccine for treatment or prophylaxis of a condition where an enhancement of a Th1-mediated immune response and suppression of a Th2/Th17-mediated immune response are desired; and
(ii) at least one interferon alpha subtype selected from IFN-α10, IFN-α14 and a hybrid thereof, in particular wherein the hybrid comprises the primary interferon binding sites of IFN-α10 and IFN-α14, in particular wherein the hybrid can be SEQ ID NO: 1 or a variant or fragment, as described herein.

In certain embodiments, the vaccine comprises at least one allergen capable of mediating a Th2/Th17 immune response, for example, a food allergen or a tumour antigen, in particular a tumour-associated antigen.

A further aspect of the present invention provides a pharmaceutical composition for enhancement of a Th1 mediated immune response and suppression of a Th2/Th17-mediated immune response, wherein the composition comprises a vaccine for treatment or prophylaxis of a condition where an enhancement of a Th1-mediated immune response and suppression of a Th2/Th17-mediated immune response are desired and at least one interferon alpha subtype selected from IFN-α10, IFN-α14 and a hybrid thereof, in particular wherein the hybrid comprises the primary interferon binding sites of IFN-α10 and IFN-α14, in particular wherein the hybrid can be SEQ ID NO: 1 or a fragment or variant thereof along with a pharmaceutically acceptable excipient, diluent or carrier.

In certain embodiments, the vaccine comprises at least one allergen capable of mediating a Th2/Th17 immune response, for example, a food allergen or tumour antigen, in particular a tumour-associated antigen.

In a further aspect, the present invention extends to improvements in the efficacy of vaccines, for example, anti-allergy or allergic disease vaccines or tumour or cancer vaccines, in particular genitourinary cancer vaccines, for example prostate cancer, renal cancer and or bladder cancer. A composition which comprises a vaccine for treatment or prophylaxis of a condition where an enhancement of a Th1-mediated immune response and suppression of a Th2/Th17-mediated immune response are desired, such as at least one allergen capable of mediating a Th2/Th17 immune response, and at least one interferon alpha subtype selected from IFN-α10, IFN-α14 and a hybrid thereof in particular wherein the hybrid comprises the primary interferon binding sites of IFN-α10 and IFN-α14, in particular SEQ ID NO: 1 or a variant or fragment thereof, has been surprisingly identified by the inventor as providing an unexpectedly efficacious composition for the treatment and/or prophylaxis of diseases, such as allergy or associated allergic diseases.

Accordingly, a further aspect of the present invention provides a vaccine composition comprising;

(i) a vaccine for treatment or prophylaxis of a condition where an enhancement of a Th1-mediated immune response and suppression of a Th2/Th17-mediated immune response are desired; and
(ii) at least one interferon alpha subtype selected from IFN-α10, IFN-α14 and a hybrid thereof in particular wherein the hybrid comprises the primary interferon binding sites of IFN-α10 and IFN-α14, in particular can be SEQ ID NO: 1 or a variant or fragment thereof.

In certain embodiments, the vaccine comprises at least one allergen capable of mediating a Th2/Th17 immune response, for example, a food allergen or a tumour antigen, in particular a tumour-associated antigen.

A further aspect of the present invention provides a vaccine composition for use in the treatment and/or prophylaxis of allergy or cancer, in particular genitourinary cancer, for example prostate cancer, renal cancer or bladder cancer, where an enhancement of a Th1-mediated immune response and the suppression of a Th2/Th17-mediated immune response are desired, said vaccine composition comprising;
(i) at least one allergen capable of mediating a Th2/Th17 immune response; and
(ii) at least one interferon alpha subtype selected from IFN-α10, IFN-α14 and a hybrid thereof in particular a hybrid IFN-α10 and IFN-α14 subtype, for example SEQ ID NO:1 or a variant or fragment, as described herein.

A further aspect of the present invention provides for the use of a vaccine composition comprising at least one allergen capable of mediating a Th2/Th17 immune response and at least one interferon alpha subtype selected from IFN-α10, IFN-α14 and a hybrid thereof in particular wherein the hybrid comprises the primary interferon binding sites of IFN-α10 and IFN-α14, in particular wherein the hybrid can be SEQ ID NO: 1 or a variant or fragment thereof, in the preparation of a medicament for the treatment and/or prophylaxis of allergy or associated allergic diseases, or cancer, in particular genitourinary cancer, for example prostate cancer, renal cancer or bladder cancer.

A further aspect of the present invention provides a method for the treatment and/or prophylaxis of allergy or associated allergic diseases or of cancer, in particular genitourinary cancer for example prostate cancer, renal cancer or bladder cancer the method comprising the step of:
administering a therapeutically effective amount of a vaccine composition or an immunogenic composition which comprises at least one allergen capable of mediating a Th2/Th17 immune response and at least one interferon alpha subtype selected from IFN-α10, IFN-α14 and a hybrid thereof, in particular wherein the hybrid comprises the primary interferon binding sites of IFN-α10 and IFN-α14, in particular wherein the hybrid can be SEQ ID NO: 1 or a fragment or variant thereof to a subject in need thereof.

According to a further aspect of the present invention, there is provided a method for the treatment and/or prophylaxis of a condition mediated by enhanced expression of IL-17, said method comprising the step of:
administering to a subject in need thereof a therapeutically effective amount of at least one interferon alpha subtype selected from IFN-α10, IFN-α14 and a hybrid thereof in particular wherein the hybrid comprises the primary interferon binding sites of IFN-α10 and IFN-α14, in particular SEQ ID NO: 1 or a fragment or variant thereof.

According to a further aspect of the present invention, there is provided at least one interferon alpha subtype comprising or consisting of an IFN-α10 and IFN-α14 hybrid in particular wherein the hybrid comprises the primary interferon binding sites of IFN-α10 and IFN-α14, in particular SEQ ID NO: 1 or a variant or fragment thereof for use in the treatment and/or prophylaxis of a condition mediated by enhanced expression of IL-17.

Suitably, in aspects and embodiments of the invention, the hybrid may comprise or consist of the amino acid sequence of SEQ ID NO: 1.

According to a further aspect of the present invention, there is provided use of at least one interferon alpha subtype IFN-α10 and IFN-α14 hybrid in particular wherein the hybrid comprises the primary interferon binding sites of IFN-α10 and IFN-α14, in particular SEQ ID NO: 1 or a variant or fragment thereof, in the preparation of a medicament for the treatment and/or prophylaxis of a condition mediated by enhanced expression of IL-17.

According to a further aspect of the present invention, there is provided a method for modulating an immune response, said method comprising the step of:
 (i) administering to a subject in need thereof a therapeutically effective amount of at least one interferon alpha subtype IFN-α10 and IFN-α14 hybrid, wherein the hybrid comprises the primary interferon binding sites of IFN-α10 and IFN-α14, and in particular can be SEQ ID NO: 1 or a variant or fragment thereof.

According to a further aspect of the present invention, there is provided at least one interferon alpha subtype IFN-α10 and IFN-α14 hybrid, wherein the hybrid comprises the primary interferon binding sites of IFN-α10 and IFN-α14, and in particular can be SEQ ID NO: 1 or a variant or fragment thereof for use in modulating an immune response.

According to a further aspect of the present invention, there is provided use of at least one interferon alpha subtype hybrid IFN-α10 and IFN-α14 subtype, wherein the hybrid comprises the primary interferon binding sites of IFN-α10 and IFN-α14, and in particular SEQ ID NO: 1 or a variant or fragment thereof in the preparation of a medicament for modulating an immune response.

In certain embodiments of the aspects of the invention outlined above, the at least one interferon alpha subtype is provided for simultaneous, separate or sequential administration with a vaccine for treatment or prophylaxis of the condition where an enhancement of a Th1-mediated immune response and suppression of a Th2/Th17-mediated immune response are desired, for example, a vaccine for the treatment or prophylaxis of a condition mediated by enhanced expression of IL-17, e.g. an inflammatory disease or condition or an autoimmune disease, such as inflammatory bowel disease (IBD), ulcerative colitis (UC) or Crohn's disease (CD), cancer, suitably hepatic cancer, lung cancer, in particular non-small cell lung cancer, ovarian cancer, breast cancer, skin cancer, melanoma or genitourinary cancer, in particular genitourinary cancer, for example prostate cancer, renal cancer or bladder cancer. In certain embodiments, the vaccine composition comprises at least one antigen. In certain embodiments, the vaccine comprises at least one allergen capable of mediating a Th2/Th17 immune response there against, for example, a food allergen.

In certain embodiments the antigen can be a tumour antigen in particular a tumour specific and/or a tumour-associated antigen.

In certain embodiments of the aspects of the invention outlined above, the at least one IFN-α subtype comprises, consists of or is an IFN-α10 IFN-α14 hybrid such as a fusion protein, or recombinant protein or the like which includes the primary interferon receptor binding sites of IFN-α10 and IFN-α14, and in particular which comprises or consists of the amino acid sequence SEQ ID NO: 1 or a variant or fragment thereof. In embodiments the IFN-α10 IFN-α14 hybrid can be glycosylated. Suitably the IFN-α10 IFN-α14 hybrid can be glycosylated in a similar fashion to IFN-α14.

In certain embodiments of the aspects of the invention outlined above, the at least one allergen is at least one food allergen or a tumour specific or tumour-associated tumour allergen, for example a prostate cancer allergen, a renal cancer allergen and or bladder cancer allergen. In certain embodiments, the at least one allergen is a dietary allergen such as food, an environmental allergen such as the venom of stinging insects, or a medication.

In a further aspect of the invention there is provided a recombinant polypeptide comprising or consisting of SEQ ID NO:1 or a fragment or variant thereof. Nucleic acid sequences derived from the amino acid sequence SEQ ID NO:1 are provided as SEQ ID NO: 2 and SEQ ID NO:3 respectively. These nucleic acid sequences can form additional aspects to the invention.

In certain embodiments of the aspects of the invention outlined above, the at least one food allergen is selected from the group consisting of, but not limited to, corn, garlic, oats, coffee, chocolate, pickle, wheat or gluten and their products or derivatives which include durum wheat, spelt (*triticum spelta*), kamut (*triticum poloncium*), couscous, bran, wheat bran, wheat germ, wheat gluten, farina, rusk, semolina, durum wheat semolina, flour, wholewheat flour, wheat flour, wheat starch, starch, modified starch, hydrolysed starch, food starch, edible starch, vegetable starch, vegetable gum, vegetable protein, cereal filler, cereal binder, cereal protein; tree nuts (including almonds, cashews, macademia, walnut and brazil nuts); seeds, including sesame, sunflower and poppy seeds; dairy derived antigens, such as milk or milk derivatives, including cheese and yoghurt; fish or shellfish or their derivatives, including from the mollusc phylum (gastropod class: snails and abalone; bivalve class: clam, mussel and oyster; cephalopod class: octopus, squid and scallop), arthropod phylum (crustacean family: crab, lobster, shrimp, prawn and crayfish) or chordate phylum (cartilaginous family: ray and shark; bony fish: cod, salmon and tuna); eggs or egg derivatives; monosodium glutamate (MSG); sulphites or sulphur dioxide; legume allergies to the leguminosae family, which includes peanut, soya (soybean or soya derivatives), bean seeds, peas, green beans, lentils, carob and liquorice; other vegetable allergies such as potato; fruit allergies to the rosaceae family, which includes apple, pear, cherry, peach and plum; fruit allergies to the cucurbitaceae family, which includes cucumber, melon, watermelon, zucchini and pumpkin; and other fruit allergies such as those developed against kiwi, banana, avocado, tomatoes, strawberries and raspberries.

In certain embodiments, the vaccine or vaccine composition can be a vaccine composition for the treatment or prophylaxis of a condition mediated by enhanced expression of IL-17, e.g. an inflammatory disease or condition or an autoimmune disease, such as inflammatory bowel disease (IBD), ulcerative colitis (UC) or Crohn's disease (CD), or cancer, suitably hepatic cancer, lung cancer, non-small cell lung cancer, ovarian cancer, breast cancer, skin cancer, melanoma or genitourinary cancer, in particular genitourinary cancer, for example prostate cancer, renal cancer or bladder cancer. In certain embodiments, the vaccine or vaccine composition can be a vaccine composition for the treatment or prophylaxis of an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired can be a condition mediated by enhanced expression of IL-17, e.g. an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired can be an inflammatory disease, in particular an inflammatory disease which is mediated by an exaggerated or overactive Th17 immune response. In certain embodiments of the aspects of the invention outlined above, the condition where an enhancement of a Th1-mediated immune response and the suppression of a Th2/Th17-mediated immune response are desired can be an autoimmune disease, in particular an autoimmune disease which is mediated by an exaggerated or overactive Th17 immune response. For example, in certain embodiments the condition can be inflammatory bowel disease (IBD), such as ulcerative colitis (UC) or Crohn's disease (CD). In certain embodiments, the condition can be selected from the group consisting of asthma, allergic rhinitis, atopic dermatitis and food allergy. In certain embodiments, the condition is cancer, in particular a genitourinary cancer, in particular prostate cancer, bladder cancer or renal cancer.

In certain embodiments of the aspects of the invention outlined above, the condition where an enhancement of a Th1-mediated immune response and the suppression of a Th2/Th17-mediated immune response are desired is an allergy or associated allergic diseases and conditions caused thereby, or cancer wherein an immune response is desired against a tumour-associated antigen, in particular a tumour associated antigen of prostate cancer, renal cancer or bladder caner. In particular, in certain embodiments the condition is a food allergy including food associated or derived allergies and associated allergic diseases and conditions caused thereby.

In certain embodiments, the food allergy associated allergic diseases or conditions include, but are not limited to, milk/dairy allergy, including Heiner syndrome, egg allergy, soya allergy, fish (shellfish) allergy, peanut and tree nut allergy, sesame and other seed allergy, wheat and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

In certain embodiments of the present invention, the method of administration is oral administration. In certain embodiments, the method of administration is sublingual or buccal administration. In certain embodiments, the method of administration involves placing a lozenge under the patient's tongue. In certain embodiments, the route of administration is ocular or by means of introduction into the nasal cavity, by way of nasal administration. Also it may be introduced by oral administration (swallowing) of a capsule or similar device into the small intestine/duodenum such that the capsule does not dissolve in the stomach, but bypasses same and delivers/releases the interferon alpha subtype only into the small intestine/duodenum.

DETAILED DESCRIPTION OF THE INVENTION

The inventor of the present invention has surprisingly discovered that administering an IFN-α subtype selected from IFN-α10, IFN-α14 and a hybrid thereof in particular a hybrid IFN-α10 and IFN-α14 subtype, for example SEQ ID NO:1, as described herein results in the enhancement of a Th1 T cell mediated immune response and the suppression of a Th2/Th17 T cell mediated immune response and can therefore skew the immune response towards a cell-mediated (Th1) path, whilst simultaneously suppressing the allergic (Th2/Th17) response. Surprisingly, this effect is enhanced when the IFN-α subtype is administered orally. This finding can be applied to provide an improved method and improved adjuvant composition for treating and/or preventing conditions where the enhancement of a Th1 T cell mediated immune response and/or the suppression of a Th2/Th17 T cell mediated immune response are desired, for example, inflammatory, autoimmune or allergy conditions, or cancer (including malignant conditions), in particular genitourinary cancers, in particular prostate cancer, renal cancer or bladder cancer. In particular, IFN-α10, IFN-α14 or a hybrid thereof in particular wherein the hybrid comprises the primary interferon binding sites of IFN-α10 and IFN-α14, and in particular SEQ ID NO: 1 or a fragment or variant thereof may be used as an adjuvant in vaccines to boost immune response to antigens and direct the immune response towards a Th1 immune response.

The inventor has also discovered that a combination of a vaccine composition or a food or tumour specific or tumour-associated antigen allergen which is capable of mediating a Th2/Th17 immune response and an IFN-α subtype selected from IFN-α10, IFN-α14 and a hybrid thereof in particular a hybrid comprising the primary interferon binding sites of IFN-α10 and IFN-α14, and in particular SEQ ID NO: 1 or a fragment or variant thereof can result in the activation of a Th1 T cell mediated immune response and the suppression of a Th2/Th17 T cell mediated immune response.

Tumour progression in normal immunocompetent subjects may reflect a failure of the immune system to recognize the tumour antigens or a subversion of the anti-tumour immune response through induction and activation of regulatory T cells. In subjects with hepatic choriocarcinoma (HCC) studies of IL-17 α cells have suggested a potential pro-tumour role for IL-17. Increased IL-17 producing cell density within the tumours of HCC patients correlates with both microvessel density and poor prognosis. Further, in subjects with non-small cell lung and ovarian cancer, higher levels of IL-17 within the tumour correlated with higher blood vessel density and shorter survival. Additionally IL-17 has been suggested to have pro-angiogenic roles and this has not been restricted to particular cell populations. Moreover, it has been shown that IL-17A or IL-17A producing cells are elevated in the environment of breast tumours and correlate with poor prognosis.

Isolation of tumour infiltrating lymphocytes (TILS) from breast cancer biopsies revealed these cells secreted significant amounts of IL-17A, and that recombinant IL-17A recruits the MAPK pathway by upregulating phosphorylated ERK 1/2 in human breast cancer lines thereby promoting proliferation and resistance to conventional chemotherapeutic agents such as Docetaxel. IL-17A has also been indicated to stimulate migration and invasion of breast cancer cells. Importantly IL-17A-neutralizing antibodies abrogated these effects, demonstrating the pathophysiological role of IL-17A as a potential therapeutic target for breast cancer. The determination by the inventor or means thus to activate a Th1 T cell mediated immune response and suppress a Th2/Th17 T cell mediated immune response is therefore significant and of utility in cancer. Thus, the present invention may be used for the treatment and prophylaxis of any known cancerous or malignant condition.

Moreover, the inventor has surprisingly discovered that orally administering the antigen and IFN-α subtype selected from IFN-α10, IFN-α14 and a hybrid thereof in particular a hybrid comprising the primary interferon binding sites of IFN-α10 and IFN-α14, and in particular SEQ ID NO: 1 or a fragment or variant thereof in combination as discussed herein can result in the activation of a Th1 T cell mediated immune response and the suppression of a Th2/Th17 T cell mediated immune response. A standard flu vaccine was mixed with a low dose of leukocyte-derived interferon alpha (LDA1) and orally administered to mice. The inventor noted that without the interferon, a small anti-flu antibody response was recorded in mice, which was approximately 50 times less than with an injected vaccine. With interferon-alpha, the response from the orally delivered vaccine was exactly the same as the injected vaccine. A series of buccal immunisations using a standard protein antigen and two interferons, LDA1 and an isolated subtype IFN-α14, surprisingly resulted in oral immunisation of mice to which the composition was administered. However, the inventor surprisingly noted that while the LDA1 gave a balanced response, IFN-α14 mediated only a significant humoral response. The production of IgG1 is indicative of a Th2 response (humoral immunity) and the production of IgG2a is indicative of a Th1 response (cell-mediated immunity).

The inventor, whilst not wishing to be bound by theory, has identified that the oral administration of a food allergen capable of mediating a Th2/Th17 immune response and an interferon alpha subtype selected from IFN-α10 and IFN-α14 can skew the immune response towards a cell-mediated (Th1) path, whilst simultaneously suppressing the allergic (Th2/Th17) response. Accordingly, the inventor has surprisingly shown for the first time that the co-administration of an allergen such as a food derived antigen that is causative of allergy or associated allergic diseases in a subject with certain interferon subtypes modulates the resulting immune response and skews it away from the Th2/Th17 response which would have been expected to develop against the allergen or antigen. This surprising finding provides an unexpected approach to treat or prevent allergic responses or diseases which occur in subjects as a result of allergens such as food-derived allergens.

Definitions

Subject

As herein defined, a "subject" includes and encompasses mammals such as humans, primates and livestock animals (e.g. sheep, pigs, cattle, horses, donkeys); laboratory test animals such as mice, rabbits, rats and guinea pigs; and companion animals such as dogs and cats.

Treatment/Therapy

The term "treatment" is used herein to refer to any regimen that can benefit a human or non-human animal. The treatment may be in respect of any existing inflammatory, autoimmune, allergic or allergy-associated condition and the treatment may be prophylactic (preventative treatment). Treatment may include curative or alleviative effects. Reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition. Accordingly, therapeutic and/or prophylactic treatment includes amelioration of the symptoms of a particular allergic condition or preventing or otherwise reducing the risk of developing a particular allergic condition. The term "prophylactic" may be considered as reducing the severity or the onset of a particular condition. "Therapeutic" may also reduce the severity of an existing condition.

Administration

The active ingredients used in the present invention (e.g. vaccine or allergen and IFN-α10, IFN-α14 or a hybrid thereof) in particular a hybrid IFN-α10 and IFN-α14 subtype, for example SEQ ID NO: 1, as described herein can be administered separately to the same subject, optionally sequentially, or can be co-administered simultaneously as a pharmaceutical, immunogenic or vaccine composition. In certain embodiments, the vaccine or allergen is co-administered with the interferon alpha subtype. The pharmaceutical composition will generally comprise a suitable pharmaceutical excipient, diluent or carrier selected depending on the intended route of administration.

The active ingredients can be administered to a patient in need of treatment via any suitable route. The precise dose will depend upon a number of factors, as is discussed below in more detail.

One suitable route of administration is parenterally (including subcutaneous, intramuscular, intravenous, by means of, for example a drip patch). Other suitable routes of administration include (but, are not limited to) oral, ocular, nasal, topical (including buccal and sublingual), infusion, intradermal or administration via oral or nasal inhalation, by means of, for example, a nebuliser or inhaler, or by an implant. Preferable routes of administration include (but, are not limited to) oral, buccal and sublingual. The compositions of the invention may also be administered in such a manner that they are directed to, or released in, specific areas of the gut intestinal tract (such as the small intestine/duodenum). Typically such release will occur after passage through the stomach, this targeted release being achievable through the use of coatings and the like.

For intravenous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

The compositions of the present invention for oral administration may be in tablet, capsule, lozenge, powder or liquid form. Oral administration may involve placing a lozenge under the tongue of the patient. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions of the present invention may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H.C. et al. 7th Edition ISBN 0-683305-72-7, the entire disclosures of which are herein incorporated by reference.

Pharmaceutical Compositions

As described above, the present invention extends to a pharmaceutical composition for the treatment of inflammatory diseases, autoimmune diseases and allergy such as food allergy and associated allergic diseases and, in particular, for the induction of a Th1 immune response and the suppression or inhibition of a Th2/Th17 immune response.

Pharmaceutical compositions according to the present invention, and for use in accordance with the present invention, may comprise, in addition to an active ingredient, a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example, oral, intravenous, intranasal or via oral or nasal inhalation. The formulation may be a liquid, for example, a physiologic salt solution containing non-phosphate buffer at pH 6.8-7.6, or a lyophilised or freeze-dried powder.

Dose

The composition is preferably administered to an individual in a "therapeutically effective amount" or a "desired amount", this being sufficient to show benefit to the individual. As defined herein, the term an "effective amount" means an amount necessary to at least partly obtain the desired response, or to delay the onset or inhibit progression or halt altogether the onset or progression of a particular condition being treated. The amount varies depending upon the health and physical condition of the subject being treated, the taxonomic group of the subject being treated, the degree of protection desired, the formulation of the composition, the assessment of the medical situation and other relevant factors. It is expected that the amount will fall in a relatively broad range, which may be determined through routine trials. Prescription of treatment, e.g. decisions on dosage etc., is ultimately within the responsibility and at the discretion of general practitioners, physicians or other medical doctors, and typically takes account of the disorder to be treated, the condition of the individual patient, the site of delivery, the method of administration and other factors known to practitioners. The optimal dose can be determined by physicians based on a number of parameters including, for example, age, sex, weight, severity of the condition being treated, the active ingredient being administered and the route of administration. A broad range of doses may be applicable. Considering oral administration to a human patient, for example, from about 10 μg to about 1000 μg of agent may be administered per human dose, optionally for 3 to 4 doses. Dosage regimes may be adjusted to provide the optimum therapeutic response and reduce side effects. For example, several divided doses may be administered daily, weekly, monthly or other suitable time intervals or the dose may be proportionally reduced as indicated by the exigencies of the situation.

Unless otherwise defined, all technical and scientific terms used herein have the meaning commonly understood by a person who is skilled in the art in the field of the present invention.

Autoimmune Disease

The term "autoimmune disease" as used herein is understood to mean any disease or condition which is caused by a body's tissues being attacked by its own immune system.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

The present invention will now be exemplified with reference to the following non-limiting figures and examples which are provided for the purpose of illustration and are not intended to be construed as being limiting on the present invention. Other embodiments of this invention will be apparent to those of ordinary skill in the art in view of this description.

BRIEF DESCRIPTION OF THE FIGURES

FIG. 9 shows the IFN-α10 and IFN-α14 hybrid amino acid sequence which contains the 2 interferon receptor (IFNaR1 and IFNaR2) binding sites.

FIG. 10 shows the reverse translation to provide the nucleic acid sequence for the IFN-α10/14 hybrid sequence based on the most likely codons.

FIG. 11 shows the reverse translation of the amino acid sequence to provide the nucleic acid sequence using consensus codons.

EXAMPLE 1

Identification of Interferon-alpha Subtypes that are Immunological Adjuvants

50 µg ovalbumin and $10^5$ IU of interferon subtypes IFN-α14, IFN-α2, IFN-α21, IFN-α10, an IFN "mix" (including IFN-α1, IFN-α8, IFN-α21 and possibly IFN-α17), IFN-α8, Intron A, MULTIFERON™ and IFN-α1 in 50 µl were administered via intraperitoneal injection three times per week to BALB-c female mice, in groups of 10.

The serum concentrations of IgG1 mg/ml (Th2 response—humoral immunity to the ovalbumin antigen) and IgG2a mg/ml (Th1 response—cell-mediated immunity to the ovalbumin antigen) were measured by ELISA.

Figure 1:
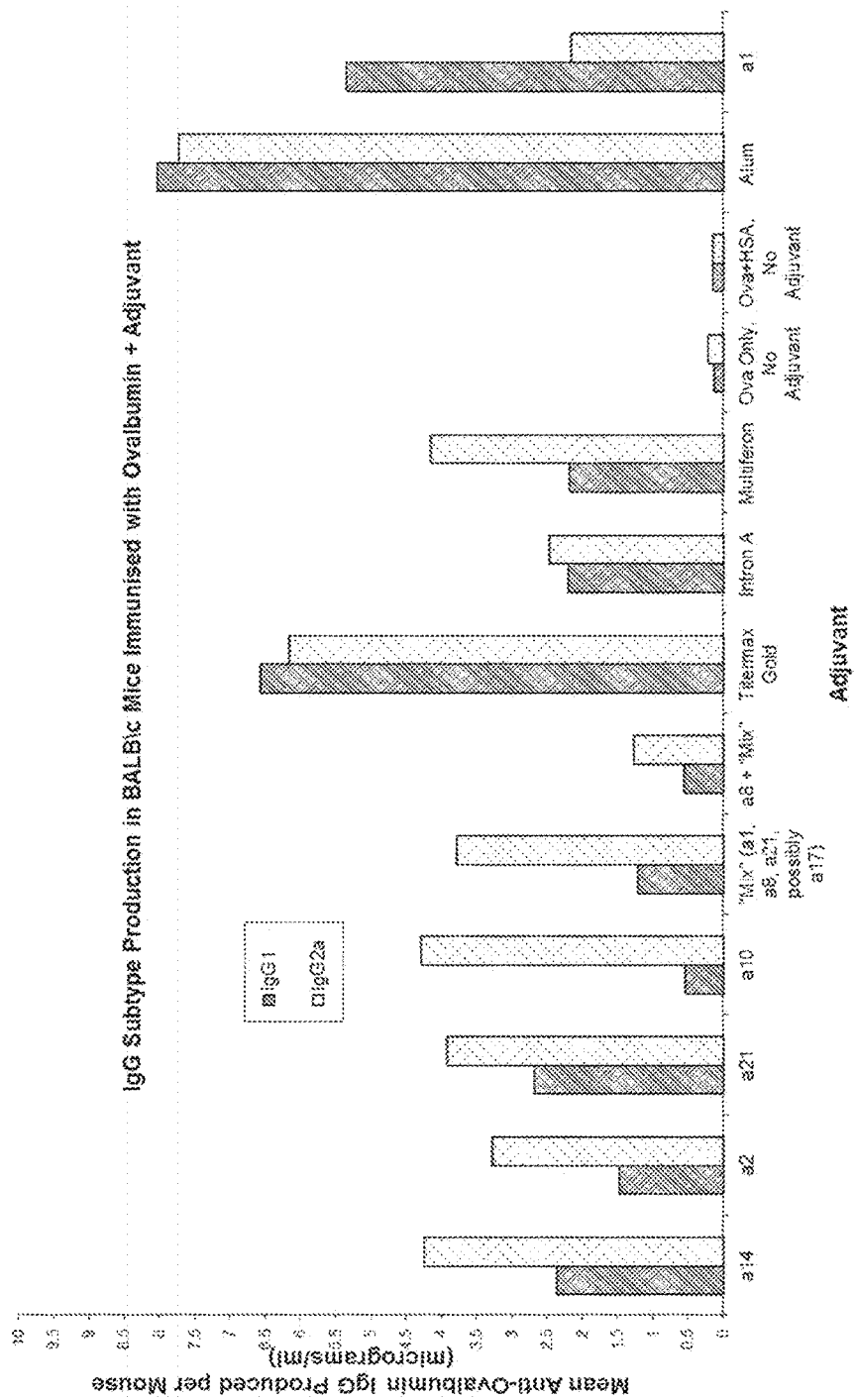
FIG. 1 shows a graph of IgG subtype (IgG1 and IgG2a) production in BALB-c mice immunised with ovalbumin and different subtypes of IFN-α.
Figure 2:
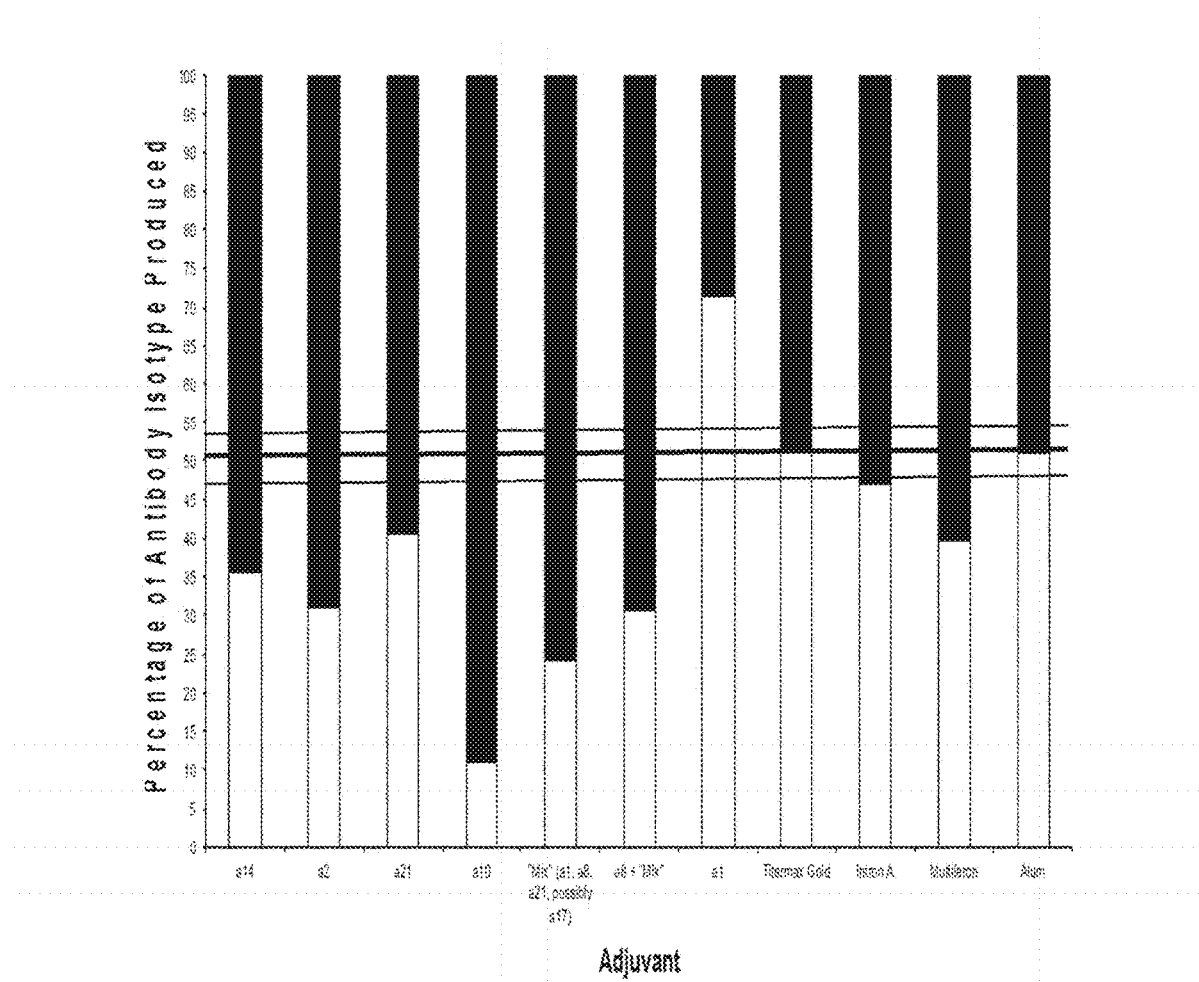
FIG. 2 shows a graph of the percentage of IgG subtype (IgG1 and IgG2a) produced in BALB-c mice immunised with ovalbumin and different subtypes of IFN-α.
Figure 3:
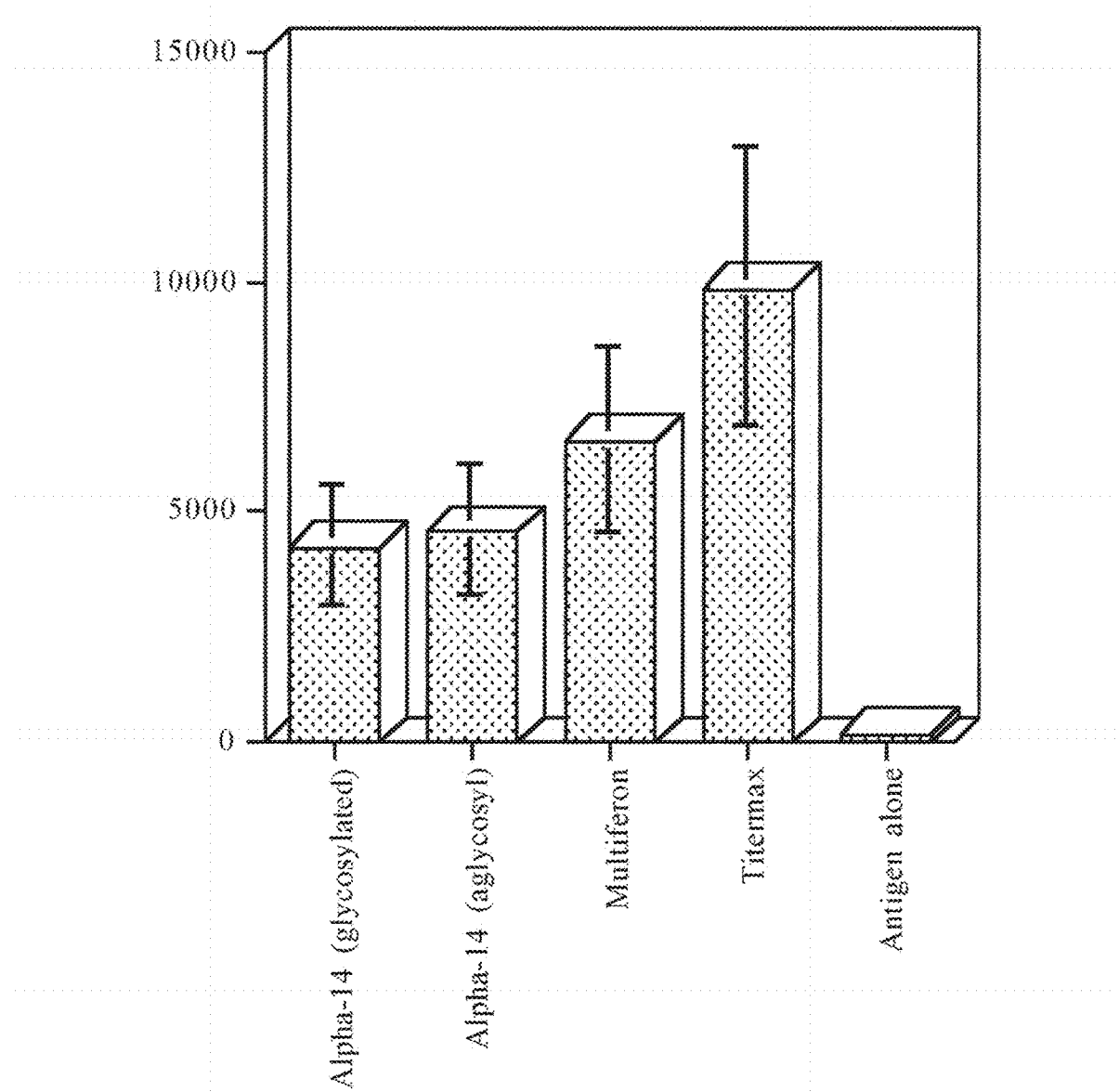
FIG. 3 shows a graph of IgG2a production in BALB-c mice immunised with ovalbumin and MULTIFERON™, glycosylated IFN-α14 and non-glycosylated IFN-α14 administered via intraperitoneal injection.
Figure 4:
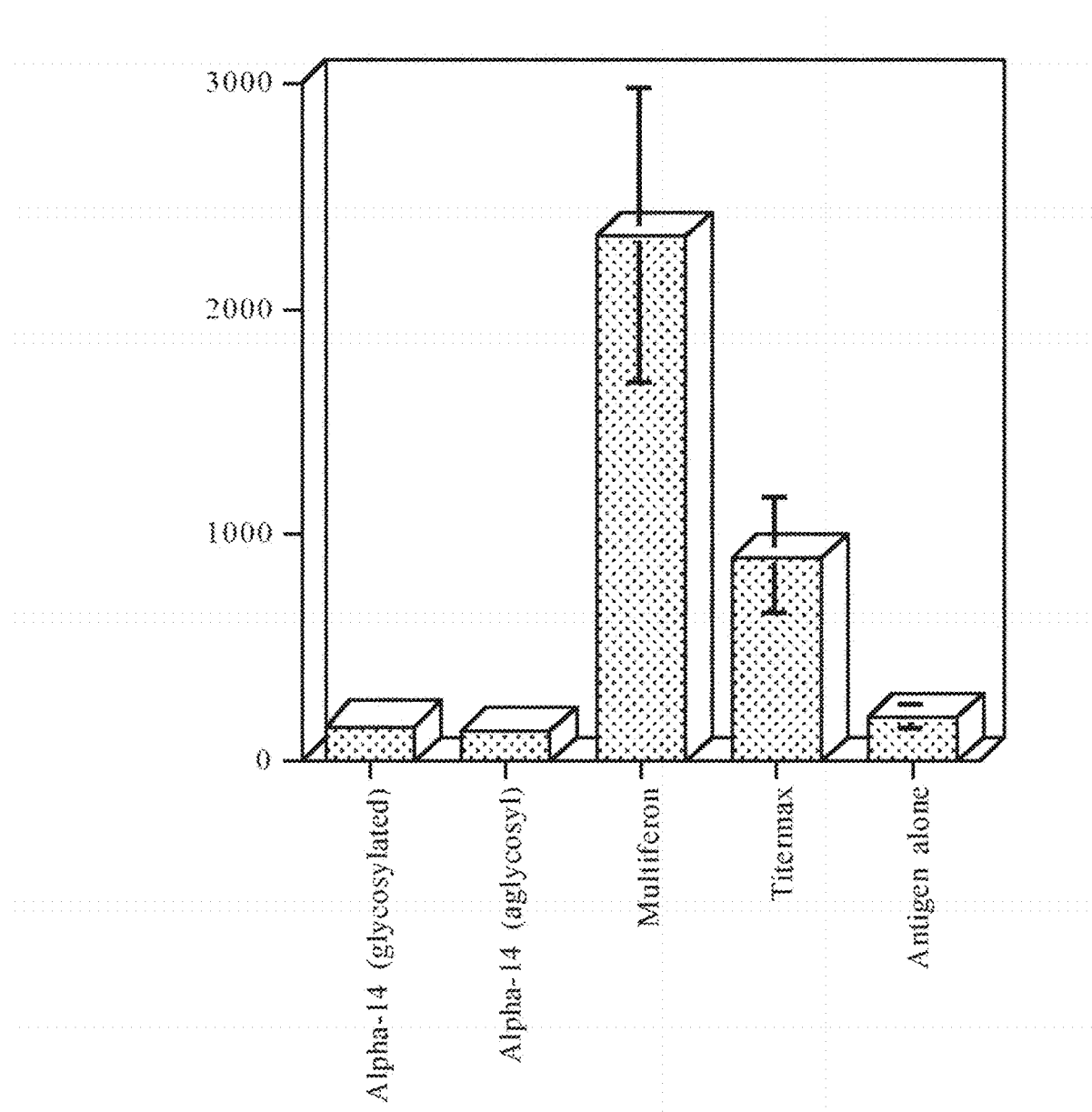
FIG. 4 shows a graph of IgG1 production in BALB-c mice immunised with ovalbumin and MULTIFERON™, glycosylated IFN-α14 and non-glycosylated IFN-α14 administered via intraperitoneal injection.
Figure 5:
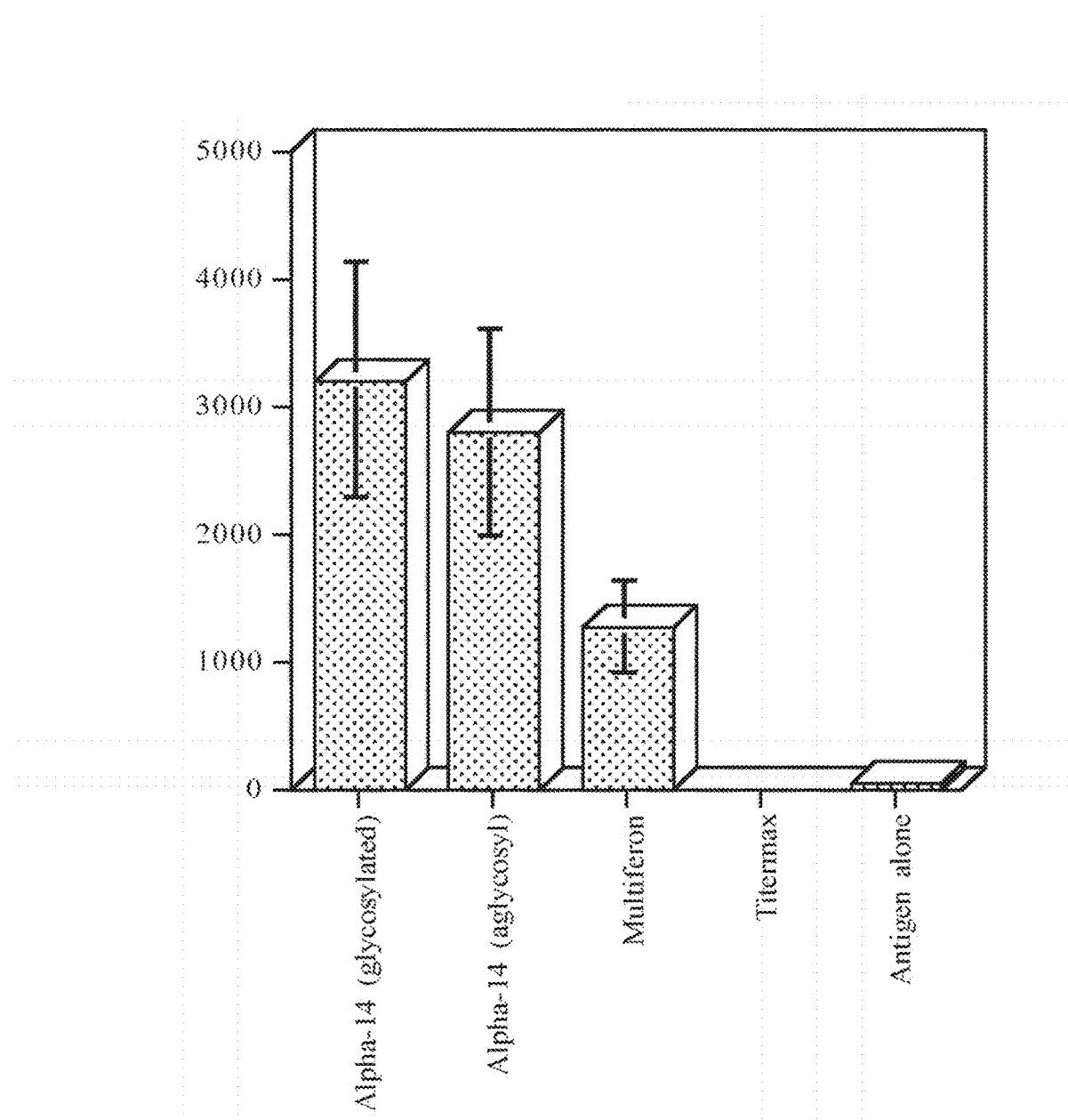
FIG. 5 shows a graph of IgG2a production in BALB-c mice immunised with ovalbumin and MULTIFERON™, glycosylated IFN-α14 and non-glycosylated IFN-α14 administered orally.
Figure 6:
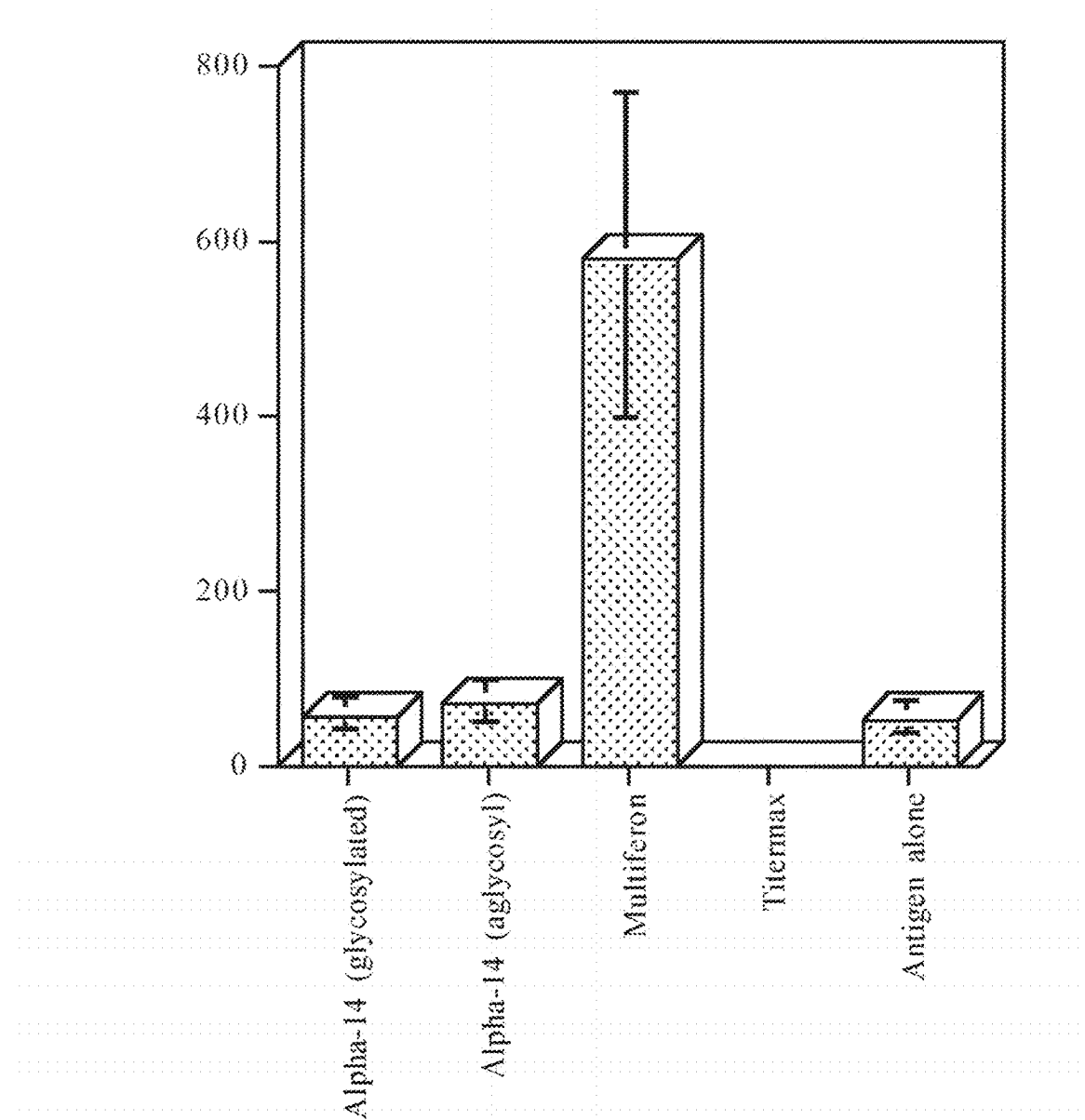
FIG. 6 shows a graph of IgG1 production in BALB-c mice immunised with ovalbumin and MULTIFERON™, glycosylated IFN-α14 and non-glycosylated IFN-α14 administered orally.

FIGS. 1 and 2 show the anti-ovalbumin IgG subtype production in BALB-c mice treated with IFN-α14, IFN-α2, INF-α21, IFN-α10, a "mix" of IFN-α1, IFN-α8, IFN-α21 and possibly IFN-α17), IFN-α8, Intron A, MULTIFERON™, ovalbumin only, ovalbumin plus human serum albumin (used as a carrier in interferon preparations) and IFN-α1.

The inventor demonstrated that IFN-α10 and IFN-α14 enhanced the production of IgG2a antibodies significantly which is indicative of an enhanced Th1 immune response. The inventor also demonstrated that IFN-α10 in particular showed low production of IgG1 antibody which is indicative of suppressing a Th2/Th17 immune response.

EXAMPLE 2

Identification of Antibody Response in BALB-c Mice after Administration of a Composition Comprising a Flu Vaccine and a Low Dose of Leukocyte Derived Interferon-alpha (LDA1)

The standard flu vaccine was mixed with a low dose ($10^5$ IU) of leukocyte derived interferon alpha (LDA1). Without the interferon, a small anti-flu antibody response was recorded in mice, approximately 50 times less than with an injection. With interferon-alpha, the response from the orally delivered vaccine was exactly the same as the injected vaccine. A series of buccal immunisations were carried out using a standard protein antigen (ovalbumin). Two interferons were compared, namely, the LDA1 and an isolated subtype, IFN-α14. Both produced a remarkable oral immunisation of the mice, but whereas the LDA1 gave a balanced response, the IFN-α14 gave only a significant humoral response. The production of IgG1 is indicative of a Th2/Th17 response (humoral immunity) and the production of IgG2a is indicative of a Th1 response (cell-mediated immunity).

EXAMPLE 3

The Identification of IFN-alpha as an Oral Immunological Adjuvant

50 µg ovalbumin and $10^5$ IU of interferon subtypes, namely MULTIFERON™, glycosylated IFN-α14 and non-glycosylated IFN-α14, in 50 µl doses were administered three times a week to BALB-c female mice via oral (buccal) and intraperitoneal injection administration.

The controls used were antigen alone and Titermax—Titermax is a mixture of compounds used in antibody generation and vaccination to stimulate the immune system to recognise an antigen given together with the mixture. Titermax is a recently developed immune adjuvant deemed to be safe in animals.

Serum concentrations (mg/ml) of IgG1 (indicative of a Th2/Th17 response) and IgG2a (indicative of a Th1 response) anti-ovalbumin antibodies were quantitated by ELISA.

The production of IgG2a and IgG1 antibodies when MULTIFERON™, glycosylated IFN-α14 and aglycosyl IFN-α14 (CHO cell-derived) were administered both orally and by injection were compared (see FIGS. 3, 4, 5 and 6).

The inventor demonstrated that IFN-α14 showed pronounced immunological adjuvant activity both orally and by injection. No significant difference was seen between the glycosylated and non-glycosylated preparations.

The inventor also demonstrated that IFN-α14 only enhanced IgG2a production associated with Th1 responses by the oral route of administration. Hence IFN-α14 is an activator of cell-mediated immunity when administered orally.

MULTIFERON™ enhanced both IgG1 and IgG2a responses when administered both orally and by injection i.e. it induced both Th1 and Th2 responses significantly.

EXAMPLE 4

In Vitro Determination of the Inhibition of Humoral Immunity (Th2/Th17) by Interferon-alpha Subtypes—Analysis of Th17 Lymphocytes and Interleukin 17

A total of $2\times10^6$ human PBMCs were stimulated with lipopolysaccharide (LPS) in the absence or presence of increasing concentrations of recombinant human alpha-IFN. Supernatants were collected after 24 hours and IL-17 concentrations measured by ELISA.

Human Cell Culture

Human peripheral blood was collected from healthy volunteers and peripheral blood mononuclear cells (PBMCs) were obtained by Lymphoprep gradient centrifugation (Pierce). For PBMC experiments, $2\times10^6$ PBMCs per ml were seeded in 24-well plates and stimulated with lipopolysaccharide (LPS) from Escherichia coli 055:B5 (Sigma) or $2\times10^6$ PBMCs per mL were seeded into 24-well plates and stimulated with 5 mg/mL plate-bound anti-CD3 (clone: UCHT1) and 2.5 mg/mL anti-CD28 (clone: CD28.2). Naive T cells (CD4+CD45RA) were obtained by magnetically labeling and depletion of non-helper T-cell and memory T-cells performed according to manufacturer's instructions (Miltenyi Biotec). A total of $1\times10^5$ naive T-cells were primed in 96-well flat bottom plates coated with anti-CD3 (clone UCHT1, 2.5 mg/mL) and with anti-CD28 (clone CD28.2, 2.5 mg/mL) antibodies. After 48 h of culture, 20 IU/mL recombinant human IL-2 (Peprotech) was added to the culture.

For human Th17 differentiation, cells were supplemented with neutralising anti-IL-4 and anti-IFNγ antibodies (both from Peprotech) and with 10 ng/mL recombinant IL-1β and 50 ng/mL recombinant IL-6 (both from Peprotech). Where required, recombinant human IFNα10/14 was added to the culture. After 5 days of culture, cells were washed, transferred into new plates and expanded until day 12 in the presence of 20 IU/mL recombinant IL-2.

ELISA and Intracellular Cytokine Staining

The IL-17 producing capacity of primed Th17 cells was assessed by stimulation with 0.1 ng/ml LPS or alternatively can be assessed by the stimulation of human cells with soluble 1 mg/mL anti-CD3 (clone: OKT3) and phorbol-12-13-dibutyrate (PdBu). Concentrations of human IL-17 in cell culture supernatants were determined using commercially available antibody pairs and protein standards (R&D Systems). Absorption was determined using an ELISA reader at 450 nm. For intracellular staining of mouse IFNγ and IL-17, T-cells are stimulated with PMA and ionomycin for 5 hours. Brefeldin A is added for the final 3 h of culture. Intracellular staining can be performed with a BD Cytofix/Cytoperm kit according to the manufacturer's instructions. Cells are incubated with fluorescein isothiocyanate-labeled anti-IFNγ (clone: XMG1.2, BD Pharmingen) and Alexa Fluor 647-labeled anti-mouse IL-17A (clone: eBio17B7, eBioscience). After washing, cells are immediately analysed using Fluorescence-activated cell sorting (FACS).

Results

Figure 7:
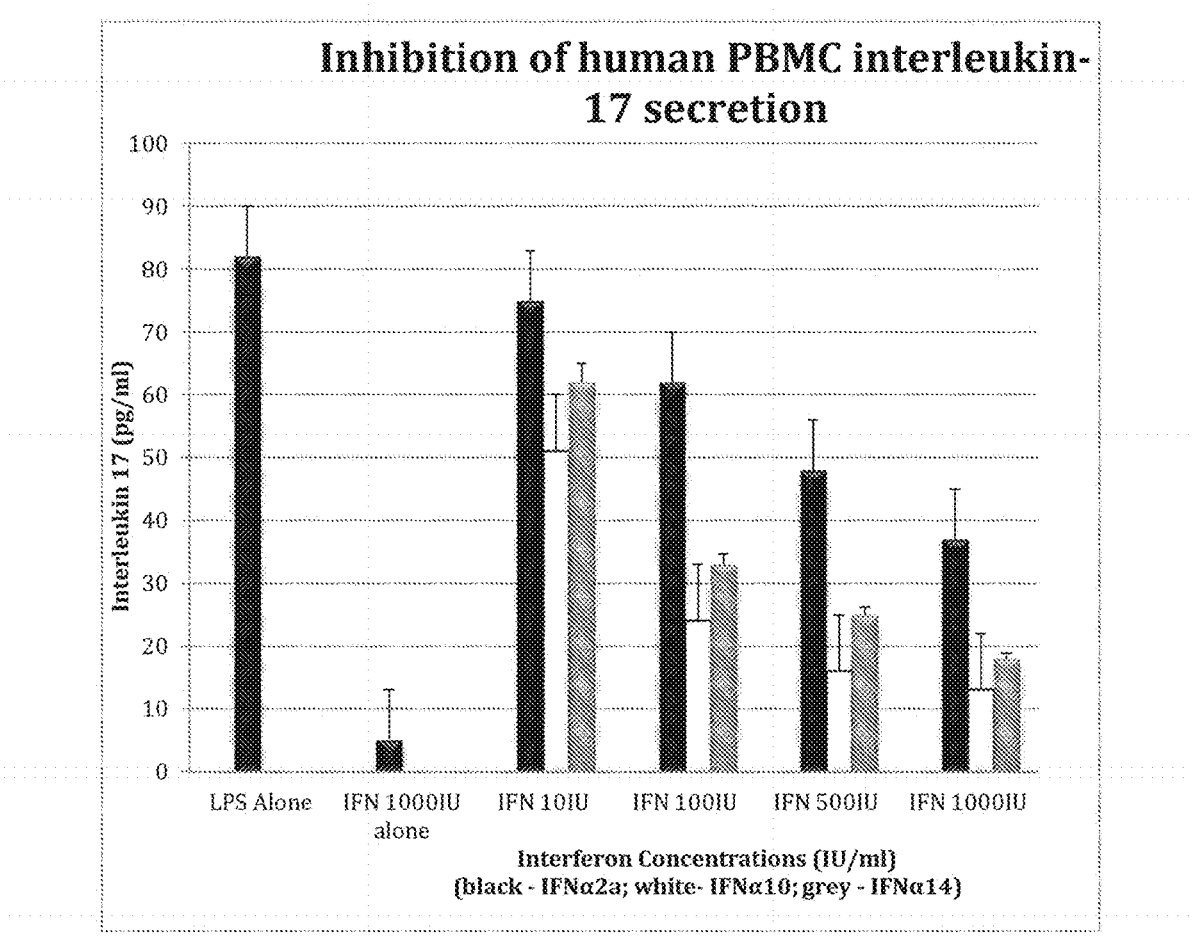
FIG. 7 shows inhibition of human PBMC interleukin-17 (IL-17) secretion with lipopolysaccharide (LPS) alone and with LPS and increasing concentrations of IFN-α2a (black), IFN-α10 (white) or IFN-14 (grey).

As shown by FIG. 7, inhibition of IL-17 was found to occur in the order IFNα10>IFNα14>IFNα2a. $P<0.05$ (FIG. 7).

EXAMPLE 5

In Vitro Determination of the Inhibition of Humoral Immunity (Th2/Th17) by Interferon-alpha Subtypes—Analysis of Th2 Cells and Associated Cytokines CRTH2 Background CRTH2 (Chemoattractant Receptor-homologous molecule expressed on Th2 cells) is a G-protein coupled receptor expressed by Th2 lymphocytes, eosinophils, and basophils. The receptor mediates the activation and chemotaxis of these cell types in response to prostaglandin D2 (PGD2), the major prostanoid produced by mast cells. PGD2 is released through mast cell degranulation in the initial phase of IgE-mediated reactions. This process is also thought to occur at the site of inflammation, such as the nasal and bronchial mucosa. Through interaction with CRTH2, PGD2 is thought to mediate recruitment and activation of CRTH2-bearing cell types to the site of the allergic reaction, in consequence amplifying and maintaining the allergic inflammation. In the nasal and bronchial mucosa, this pro-inflammatory cascade is thought to start during the so-called late allergic response occurring 3 to 9 hours after allergen challenge. The interaction between PGD2 and CRTH2 would, therefore, contribute to the so-called "Th2 polarisation", with consequent Th2 cytokine production and the typical eosinophilic and basophilic characteristics of the inflammation.

IFNα Inhibits Human CD4+ Th2 Development.

Purified human CD4+/ CD45RA+ cells were activated with plate-bound anti-CD3/anti-CD28 under defined cytokine conditions. Induction of CRTH2 expression was assessed by flow cytometry. All $P<0.05$, above 100 IU IFN compared with IL-4 alone.

Human Subjects

Peripheral blood was collected from healthy adult donors and cells purified as below.

T Cell Cultures and Analysis

Peripheral blood was obtained from healthy male adult donors and naive CD4+/CD45RA+ T cells were purified (>92%) from buffy coats by magnetic bead separation (BD Biosciences, USA). CD4+ cells were activated with plate-bound anti-CD3/anti-CD28 and IL-2 (50U/ml) in complete Iscove's Modified Dulbecco's Medium containing 10% FCS, in the presence of recombinant human recombinant IL-4 (R&D Systems, USA), at a concentration of 20 ng/ml for 7 days. Flow cytometric analysis was performed with hCD294 (chemo-attractant receptor homologous molecule expressed on Th2 cells [CRTH2])-Alexa 647 (BD Biosciences).

Results

Figure 8:
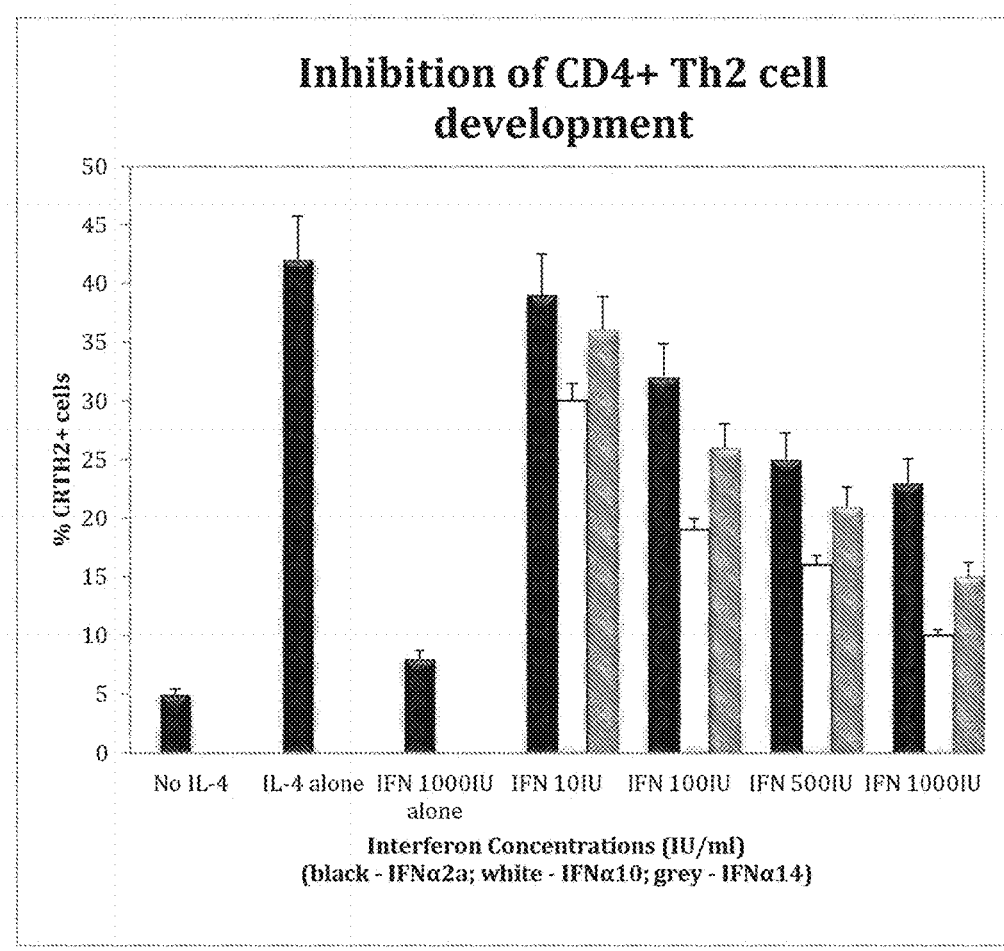
FIG. 8 shows the inhibition of Interleukin-4 (IL4)-induced CD4+ Th2 cell development using increasing concentrations of IFN-α2a (black), IFN-α10 (white) or IFN-14 (grey).

In humans, the PGD2 receptor, CRTH2, is selectively expressed on Th2 cells and is induced by IL-4 during Th2 development. IL-4 promoted the development of cells expressing CRTH2. However, as shown in FIG. 8 all the IFN-alphas markedly blocked IL-4 driven CRTH2 expression, in a dose-dependent manner in the order IFNα10>IFNα14>IFNα2a, thus supporting the concept that these cytokines suppress Th2 (humoral) immunity, but are recognised as potent activators of Th1-associated immunity.

Figure 12:
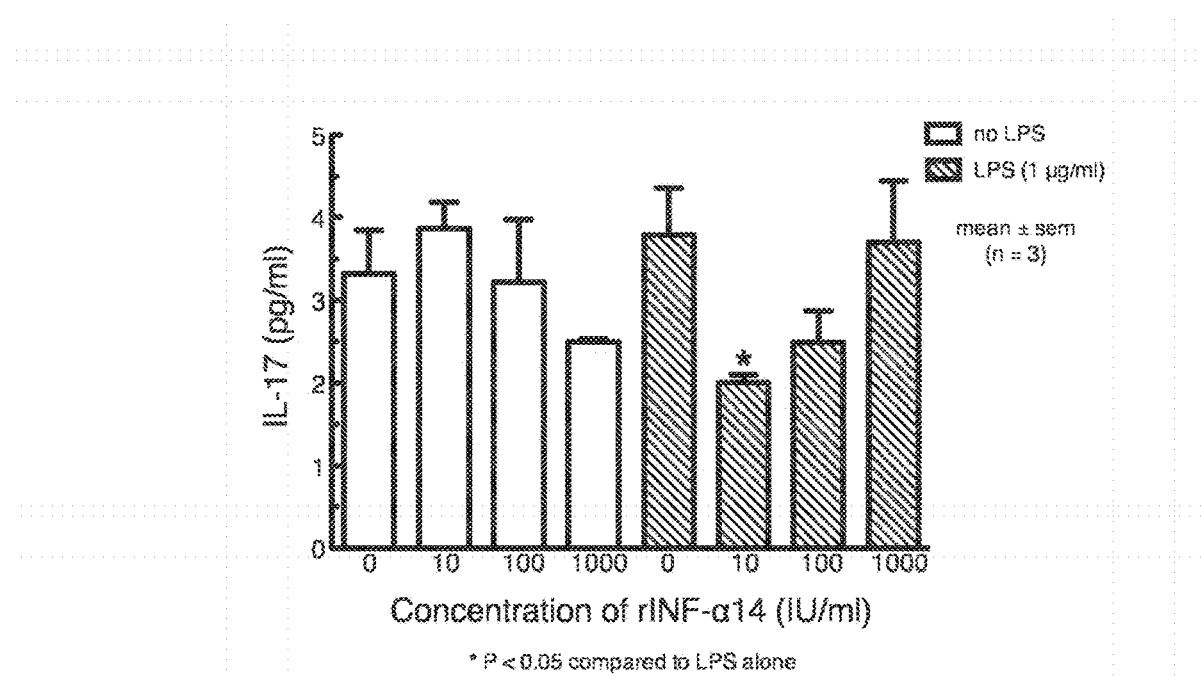
FIG. 12 indicates the effect caused by rIFN-α14 on the production of IL-17 in whole human blood incubated with one microgram E.coli lipopopolysaccharide (LPS) for 48 hours. The α-14 gave a significant suppression of IL-17 secretion. IL-α-2 and α-10 showed no significant suppression.

As shown in FIG. 12, the effect of rIFN-α14 on the production of IL-17 in human blood incubated with LPS for 48 h was tested.

Whole human blood was incubated without (open columns) or with 1 μg/m1 LPS (cross hatched columns) in the absence and presence of a range of concentrations of rIFN-α14 (0-1,000 IU/ml) for 48 h at 37° C., in an atmosphere of 5% $CO_2$ in air, in a humidified incubator. Plasma was collected by centrifugation and levels of IL-17 determined by ELISA.

FIG. 12 indicated a dose response to IFN-α14 wherein 1 mg=$10^{-8}$ IU.

Figure 13:
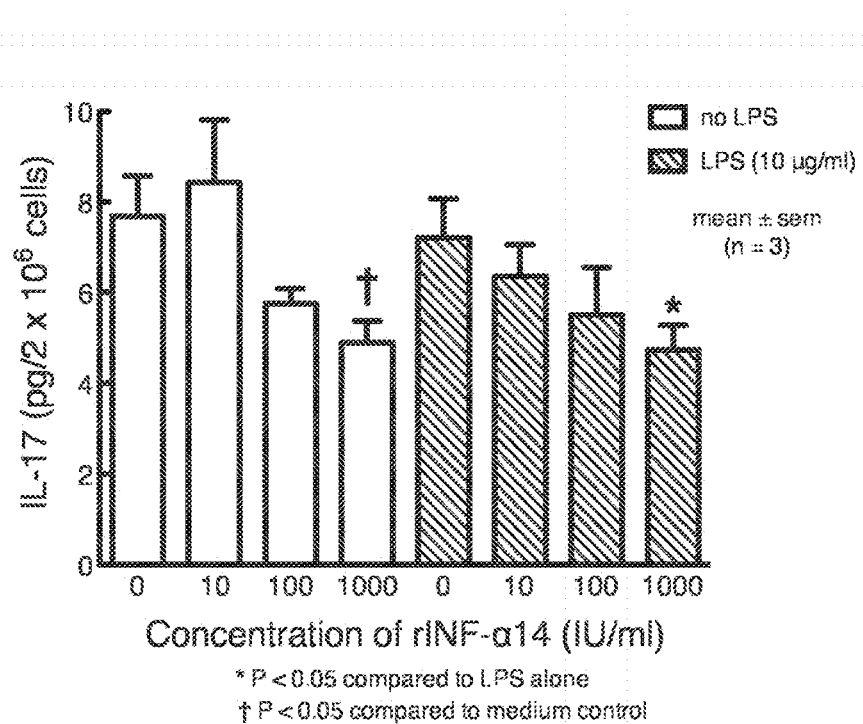
FIG. 13 shows the effect caused by rIFN-α14 on the production of IL-17 from human peripheral blood mononuclear cells incubated with 10 micrograms E. coli lipopolysaccharide (LPS) for 48 hours. The α-14 caused a significant suppression of IL-17 secretion with and without LPS activation. IL-α-2 and α-10 showed no significant changes in the IL-17 concentrations (results not shown).

As shown in FIG. 13 the effect of rIFN-α14 on the production of IL-17 in human PBMCs incubated with LPS for 48 h was tested.

Human Peripheral Blood Mononuclear cells (PBMCs), a critical component in the immune system, were isolated from whole human blood by density gradient centrifugation. $2\times10^6$ PBMCs were incubated without (open columns) or with 10 μg/ml LPS (cross hatched columns) in the absence and presence of a range of concentrations of rIFN-α14 (0-1,000 IU/ml) for 48 h at 37° C., in an atmosphere of 5% $CO_2$ in air, in a humidified incubator. Levels of IL-17 in the supernatant were determined by ELISA.

As indicated by FIG. 13, increasing concentrations of rIFN-α14 was found to reduce the IL-17 both in untreated and treated LPS cells.

Figure 14:
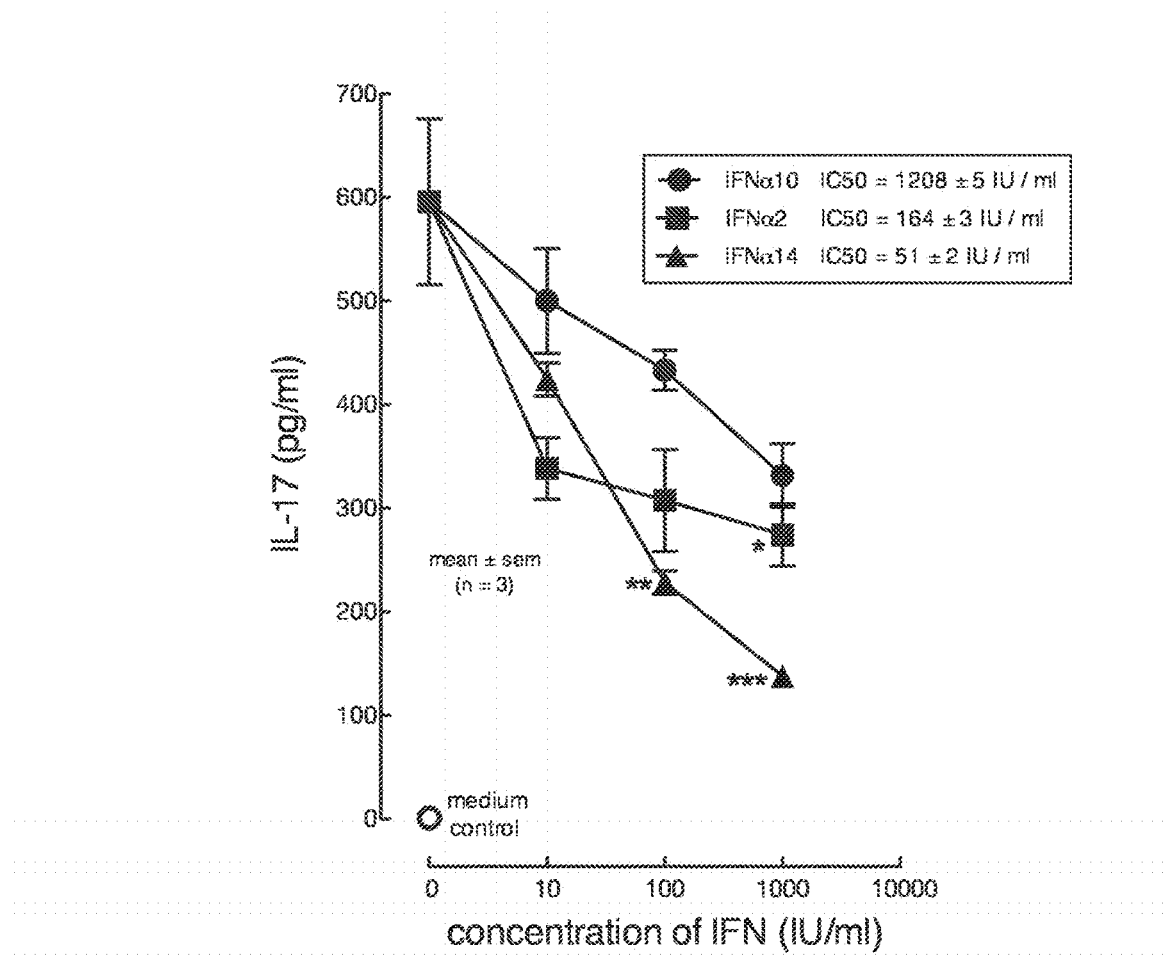
FIG. 14 shows the effect caused by rIFN-α10, rIFN-α14 and rIFN-α2 on IL-17 production by whole human blood incubated with PHA for 5 days. The α-14 is an extremely potent inhibitor (P<0.001 at 1,000 IU/ml) of IL-17 compared with the commonly available α-2; the α-10 is more than 20× less active in this context.

As shown in FIG. 14, the effect of rIFNα10, rIFNα14 and rIFN2 on IL-17 production by whole blood incubated with phytohaemagglutinin (PHA) for 5 days was tested.

Whole human blood was diluted 1/10 with RPMI 1640 culture medium and incubated without or with 100 μg/ml PHA in the absence and presence of a range of concentrations of rIFN-α14, rIFN-α10 and rIFN-α2 for 5 days at 37° C., in an atmosphere of 5% $CO_2$ in air, in a humidified incubator. At the end of this period, supernatants were aspirated and levels of IL-17 in supernatants measured by ELISA. Values represent the mean±sem, for n=3 incubations. Statistical analysis and $IC_{50}$ values were determined using GraphPad Prism 5 (GraphPad Software Inc., California, USA).

As indicated in FIG. 14 the provision of rIFN-α14 at higher concentrations (100-1000 IU/ml) caused a greater decrease in IL-17 than the provision of IFN-α12 or IFN-α10. rIFN-α14 is considered to be the most potent interferon tested at reducing IL-17 levels.

Figure 15:
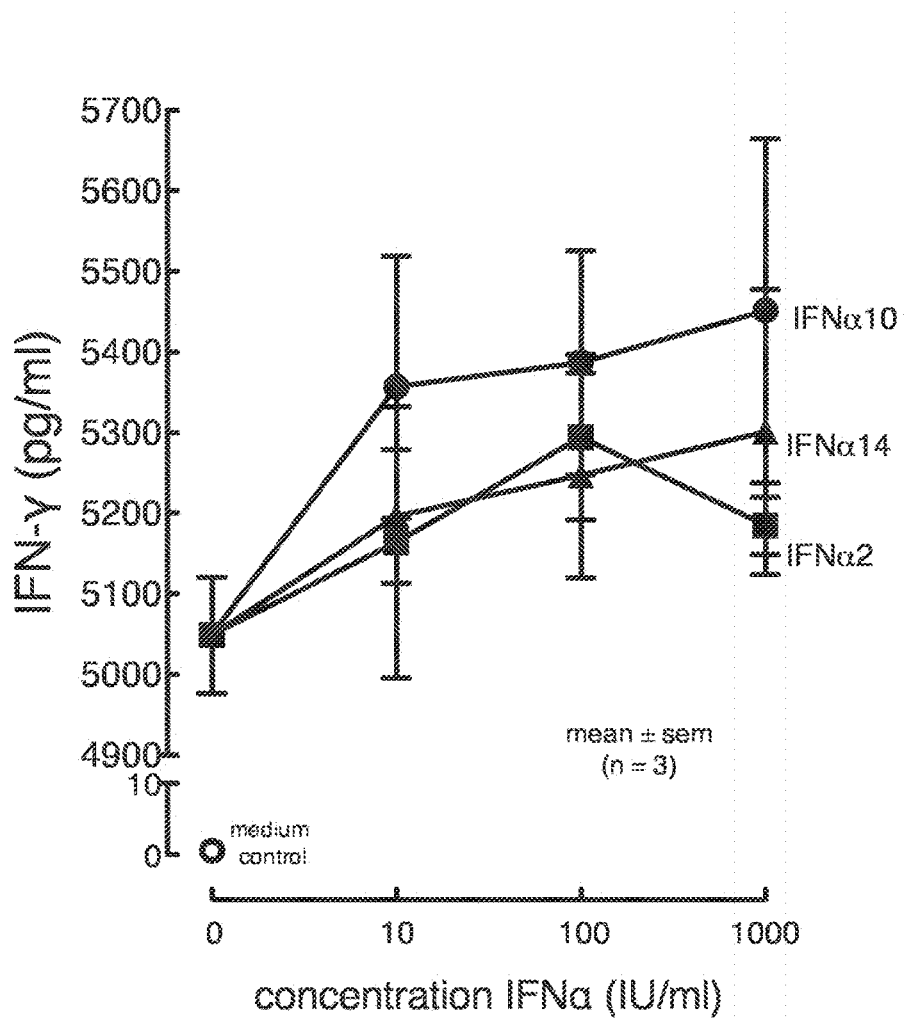
FIG. 15 shows the effect caused by rIFN-α10, rIFN-α14 and rIFN-α2 on IFN-gamma production by whole human blood incubated with PHA for 5 days. The α-10 is the most potent interferon-alpha in this context causing enhanced secretion of IFN-gamma and or IFN gamma or type 2 interferon—critical for both and innate and adaptive immunity against viruses, intracellular bacterial infections and in the control/elimination of tumours.
Figure 16:
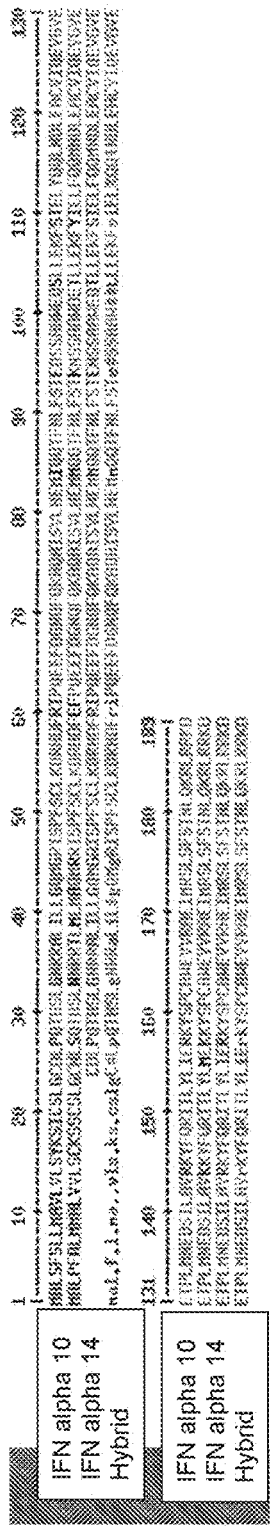
FIG. 16 illustrate a sequence alignment of IFN-αalpha10 (SEQ ID NO:4) and IFN-alpha4 (SEQ ID NO:5) amino acid sequences and the hybrid sequence SEQ ID NO: 1 discussed herein.

As shown in FIG. 15, the effect of rIFNα10, rIFNα14 and rIFNα2 on IFN-gamma production by whole blood incubated with PHA for 5 days.

Whole human blood was diluted 1/10 with RPMI 1640 culture medium and incubated without or with 100 µg/ml PHA in the absence and presence of a range of concentrations of rIFN-α10, rIFN-α14 and rIFN-α2 for 5 days at 37° C., in an atmosphere of 5% $CO_2$ in air, in a humidified incubator. At the end of this period supernatants were aspirated and levels of IFN-gamma in supernatants measured by ELISA. Values represent the mean±sem, for n=3 incubations. plasma was collected by centrifugation and levels of IFN-gamma determined by ELISA. Values represent the mean±sem, for n=3 incubations.

It was determined that rIFN-α10 was most effective of the interferons tested at promoting levels of IFN-gamma. IFN-gamma has previously been suggested to be important in providing an anti-cancer effect.

EXAMPLE 6

Effects of Human Interferon Alpha-14 and Alpha-10 on Unstimulated and Activated Human Mononuclear Leukocytes from Normal Subjects

TABLE 1

Synopsis of 400 interleukins, chemokines and protein marker estimations* following IFN-α10/14 treatment of human mononuclear cells

| ANALYTE | FOLD NUMBER OF UNSTIMULATED/ ALPHA-IFN TREATED CELLS | | FOLD NUMBER OF PHA-STIMULATED/PHA-STIMULATED ALPHA-IFN TREATED CELLS | |
|---|---|---|---|---|
| | Alpha-14 | Alpha-10 | Alpha-14 | Alpha-10 |
| CYTOKINES | | | | |
| IL-1a | 0 | +23 | 1 | +2 |
| IL-1b | 0 | +70 | −2 | 1 |
| IL-1(F5 to F10) | 0 | 0 | 0 | 0 |
| IL-2 | 0 | 0 | +7 | +4 |
| IL-3 | 0 | 0 | −11 | x |
| IL-4 | 0 | 0 | 1 | −3 |
| IL-5 | 0 | 0 | −420 | 1 |
| IL-6 | −19 | +1000 | 1 | 1 |
| IL-7 | 0 | 0 | 0 | 0 |
| IL-8 | 1 | +100 | 1 | 1 |
| IL-9 | 0 | 0 | 0 | 0 |
| IL-10 | 0 | +5 | +2 | +2 |
| IL-11 | 0 | 0 | 0 | 0 |
| IL-12 p40 | 0 | +350 | 0 | +1 |
| IL-12 p70 | 0 | 0 | +11 | 0 |
| IL-13 | 0 | 0 | −5 | 1 |
| IL-15 | 0 | 0 | 0 | 0 |
| IL-16 | 1 | 1 | 1 | 1 |
| IL-17 | 0 | 0 | −43 | −5 |
| IL-18 | 0 | 0 | 0 | 0 |

TABLE 1-continued

Synopsis of 400 interleukins, chemokines and protein marker estimations* following IFN-α10/14 treatment of human mononuclear cells

| ANALYTE | FOLD NUMBER OF UNSTIMULATED/ ALPHA-IFN TREATED CELLS | | FOLD NUMBER OF PHA-STIMULATED/PHA-STIMULATED ALPHA-IFN TREATED CELLS | |
|---|---|---|---|---|
| | Alpha-14 | Alpha-10 | Alpha-14 | Alpha-10 |
| IL-20 | 0 | 0 | 0 | 0 |
| IL-21 | 0 | x | 0 | x |
| IL-23 | +4 | +3 | +6 | 1 |
| IL-24 | 0 | 0 | 0 | 0 |
| IL-27 | 0 | 1 | 0 | 1 |
| IL-28 | 0 | 0 | 0 | 0 |
| IL-29 | 0 | 0 | 0 | 0 |
| IL-31 | 0 | 0 | 0 | 0 |
| IL-33 | 0 | 0 | 0 | 0 |
| IL-34 | 0 | 0 | 0 | 0 |
| IFN-gamma | 0 | 0 | +600 | +3000 |
| G-CSF | −1500 | +20 | 1 | 1 |
| GM-CSF | 0 | 0 | 0 | 1 |
| CD MARKERS | | | | |
| CD14 | +2 | +2 | +2 | +2 |
| CD23 | −22 | 1 | −850 | −3 |
| CD30 | 0 | 0 | 0 | 0 |
| CD40 | +2 | +2 | 1 | 1 |
| CD97 | −2 | 1 | −5 | −5 |
| CD152 (CTLA-4) | 1 | 0 | −2 | 0 |
| CD154 | 1 | x | +2 | x |
| CD163 | −2 | 1 | −2 | 1 |
| CD200 | 1 | 1 | −1 | 1 |
| CD223 (LAG3) | 0 | 0 | −3 | +3 |
| SELECTED CHEMOKINES AND PROTEINS | | | | |
| CXCL1 (GROa) | −7600 | −12 | −3400 | 1 |
| CXCL5 (ENA-78) | −6 | +16 | −32 | −3 |
| CXCL10 (IP10) | +460 | +10 | +1 | 1 |
| CCL1 (I-309) | 0 | 1 | −24 | 1 |
| CCL7 (MCP-3) | −2 | −200 | −149 | 1 |
| CCL16 (HCC-4) | 0 | 1 | −100 | 1 |
| CCL20 (MIP-3a) | −69 | +40 | −2 | 1 |
| MMP-2 (collagenase) | +600 | +200 | +450 | +500 |
| MMP-10 (pro-teoglycanase) | −121 | 1 | −2 | −2 |
| ACE-2 | +12 | 0 | +6 | 0 |
| PDGF Ralpha | −4 | −7 | −1 | −3 |
| Tie-1 | −170 | −200 | −8 | −280 |
| ICAM-1 | −1 | +2 | −3 | 1 |
| TREM-1 | +5 | −2 | +2 | −5 |
| E-SELECTIN | 1 | −7 | 1 | −2 |

0 = no analyte detected
1 = analyte present but no effect of alpha-10/14
x = not determined
The positive effect of alpha-10/14 is denoted by a +
The negative effect of alpha-10/14 interferon is denoted by a −
*The assay system used was the RayBio Quantibody Human Cytokine Array 9000 (QAH-CAA-9000 provided by Insight Bio Ltd.). This a multiplex ELISA, measuring the concentrations of 400 proteins in a single assay process, including pro- and anti-inflammatory markers, interleukins, cancer markers, chemokines, growth factors and related molecules. Human peripheral blood mononuclear leukocytes (normal blood donors) were treated with 10 ng/ml IFN-α14/10 for 4 hours prior to assay. Tests were performed on 2 groups of cells -
a) unactivated and
b) activated with PHA (phytohaemagglutinin) to induce a high level of stimulation.

Effects of Alpha-14 on Activated Immune Cells

More than 30 interleukins were quantitated but only 6 showed significant changes in the activated cells, indicating the targeted and very specific nature of the interaction of the alpha-14 with the human immune response.

Interleukin 2 increased by 7-fold, IL-12p70 +11 fold and interferon-γ +600 fold, indicating a strong proliferation of the Th1 (cell-mediated) response while a 6-fold increase in IL-23 is in keeping with its role in cell-mediated immunity and its association with IL-12.

Very large decreases were observed with IL-3 and IL-5 of 11 and 420-fold respectively. These molecules are associated with the production of myeloid cells and immunoglobulin production (humoral immunity). IL13 also decreased by 5-fold, which is important as this interleukin is implicated in the secretion of IgE, the allergy antibody. Also crucial was the 43-fold decrease in IL-17. This regulatory cytokine is increased in autoimmune diseases, humoral (antibody-mediated) immunity and stimulation of inflammation through attraction of neutrophils.

CD23 or FcεRII is a receptor for the allergy antibody, IgE, and is displayed widely on different types of leukocytes. CD23 activation controls IgE production and significant increases are seen in patients with allergic disorders. This important marker was decreased by 850-fold, in the activated cells, by alpha-14.

Effects of Alpha-14 on Non-activated Immune Cells

IL-6 decreased 19-fold. This cytokine stimulates liver protein synthesis in responses to traumas, causes increases in body temperature and is involved in muscle contraction. However, it is its essential role in antibody-mediated immunity that is important in allergy.

G-CSF was also decreased by more than 1000-fold. This molecule can stimulate the bone marrow to make increased numbers of neutrophils that could be involved in inflammation. At the same time the secretion of the chemokine CXCL1 was suppressed by 7,500-fold—this prevents it attracting neutrophils to the site of a response and causing inflammation. Also the concentration of the chemokine, CXCL10 was enhanced by 460-fold—its role is to attract T-lymphocytes to an ongoing immune response.

Effects of Alpha-10 on Activated Immune Cells

As with alpha-14, alpha-10 only regulated a small number of cytokines out of the numbers assessed. Of particular note were the increases in IL-2 and interferon-γ of 4 and 3000 fold respectively indicating a switch to cell-mediated immunity. IL-17 levels fell by 5 fold, confirming this change in balance.

The large reduction in CD23 was not evident with alpha-10 and its major effects on chemokines were on Tie-1 (tyrosine kinase crucial in the process of lymphatic remodelling) and TREM-1 (neutrophil activation) where it caused reductions of 280 and 5 fold respectively.

Effects of Alpha-10 on Non-activated Immune Cells

Alpha-10 showed significant activity in this context enhancing IL-1α/β by up to 70 fold and IL-6,8,10,12 (p40) by 1000, 100, 5 and 350 fold in keeping with a strong support for cell-mediated over humoral immunity. G-CSF was also enhanced by 20 fold in total contrast to alpha-14.

Few changes were recorded with the CD markers but CXCL1 was reduced by 12 fold while CXCL5 and 10 increased by 16 and 10 fold and CCL20 rose by 40 fold. However, CCL7 and Tie-1 fell by 200 fold each. These results are in keeping with a significant movement towards cell-mediated immunity.

Result

The low doses of interferon-alpha 14 and 10 have modified cytokine synthesis in order to enhance cell-mediated immunity at the expense of antibody-mediated immunity. This would be invaluable in enhancing the activities of certain vaccines where a humoral immune response can be detrimental e.g. viral and cancer vaccines.

In addition the results are totally in keeping with the general understanding that allergy can be alleviated by changing the immune response to an allergen by shifting an antibody response to a cellular response. Such a change would be part of acquired immunity and hence, potentially, a long-term solution by developing tolerance.

In addition, the alpha-14 significantly suppressed the capacity of leukocytes to make/utilise IgE and hence it inhibited the immediate effects of an allergic reaction, together with reducing inflammatory elements of immunity while enhancing the involvement of more control elements.

All documents referred to in this specification are herein incorporated by reference.

Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for the treatment of a condition where an enhancement of a Th1-mediated immune response and suppression of a Th2/Th17-mediated immune response are desired, and wherein the condition is cancer, said method comprising the step of:
(i) administering to a subject in need thereof a therapeutically effective amount of a hybrid of IFN-α10 and IFN-α14, wherein the hybrid includes the primary interferon receptor binding sites of IFN-α10 and IFN-α14 and has improved binding to interferon receptor 1 and interferon receptor 2 in comparison to IFN-α10 or IFN-α14, and wherein the hybrid comprises the amino acid sequence set forth by SEQ ID NO: 1.

2. The method as claimed in claim 1 wherein the cancer is hepatic cell cancer, lung cancer, non-small cell lung cancer, ovarian cancer, breast cancer, skin cancer, melanoma, genitourinary cancer, prostate cancer, renal cell cancer, or bladder cancer.

3. The method as claimed in claim 1 wherein the hybrid of IFN-α10 and IFN-α14 is administered orally.

4. The method as claimed in claim 1 wherein the method includes a step of administering to the subject a therapeutically effective amount of a vaccine composition for treatment of the condition where an enhancement of a Th1-mediated immune response and suppression of a Th2/Th17-mediated immune response are desired.

5. The method as claimed in claim 4 wherein the vaccine composition comprises at least one allergen capable of mediating a Th2/Th17 immune response.

6. The method as claimed in claim 5 wherein the at least one allergen is a tumour antigen.

7. The method as claimed in claim 4 wherein the vaccine composition is administered sequentially, separately or simultaneously with the at least one interferon alpha subtype.

* * * * *

SEQUENCE LISTING

```
<160> NUMBER OF SEQ ID NOS: 5

<210> SEQ ID NO 1
<211> LENGTH: 166
<212> TYPE: PRT
<213> ORGANISM: Homo sapiens

<400> SEQUENCE: 1

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60
```

Phe Asn Leu Phe Ser Thr Glu Asn Ser Ser Ala Ala Trp Glu Gln Thr
65                  70                  75                  80

Leu Leu Glu Lys Phe Ser Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 2
<211> LENGTH: 498
<212> TYPE: PRT
<213> ORGANISM: Homo sapiens

<400> SEQUENCE: 2

Thr Gly Cys Gly Ala Thr Cys Thr Gly Cys Cys Gly Cys Ala Gly Ala
1               5                   10                  15

Cys Cys Cys Ala Thr Ala Gly Cys Cys Thr Gly Gly Gly Cys Ala Ala
                20                  25                  30

Cys Cys Gly Cys Gly Cys Gly Cys Gly Cys Thr Gly Ala Thr Ala Thr
            35                  40                  45

Cys Thr Gly Cys Thr Gly Gly Cys Cys Ala Gly Ala Thr Gly Gly
        50                  55                  60

Gly Cys Cys Gly Cys Ala Thr Thr Ala Gly Cys Cys Gly Thr Thr
65                  70                  75                  80

Thr Ala Gly Cys Thr Gly Cys Cys Thr Gly Ala Ala Gly Ala Thr
                85                  90                  95

Cys Gly Cys Cys Ala Thr Gly Ala Thr Thr Thr Thr Cys Gly Cys Ala
            100                 105                 110

Thr Thr Cys Cys Gly Cys Ala Gly Gly Ala Ala Gly Ala Ala Thr Thr
        115                 120                 125

Thr Gly Ala Thr Gly Gly Cys Ala Ala Cys Ala Gly Thr Thr Thr
130                 135                 140

Cys Ala Gly Ala Ala Ala Gly Cys Gly Cys Ala Gly Gly Cys Gly Ala
145                 150                 155                 160

Thr Thr Ala Gly Cys Gly Thr Gly Cys Thr Gly Cys Ala Thr Gly Ala
                165                 170                 175

Ala Ala Thr Gly Ala Thr Gly Cys Ala Gly Cys Ala Gly Ala Cys Cys
            180                 185                 190

Thr Thr Thr Ala Ala Cys Cys Thr Gly Thr Thr Thr Ala Gly Cys Ala
        195                 200                 205

Cys Cys Gly Ala Ala Ala Ala Cys Ala Gly Cys Ala Gly Cys Gly Cys
    210                 215                 220

Gly Gly Cys Gly Thr Gly Gly Gly Ala Ala Cys Ala Gly Ala Cys Cys
225                 230                 235                 240

Cys Thr Gly Cys Thr Gly Gly Ala Ala Ala Ala Thr Thr Thr Cys Ala
                245                 250                 255

Gly Cys Ala Thr Thr Gly Ala Ala Cys Thr Gly Thr Thr Thr Cys Ala

```
            260                 265                 270
Gly Cys Ala Gly Ala Thr Gly Ala Ala Cys Gly Ala Thr Cys Thr Gly
            275                 280                 285

Gly Ala Ala Gly Cys Gly Thr Gly Cys Gly Thr Gly Ala Thr Thr Cys
            290                 295                 300

Ala Gly Gly Ala Ala Gly Thr Gly Gly Gly Cys Gly Thr Gly Gly Ala
305                 310                 315                 320

Ala Gly Ala Ala Ala Cys Cys Cys Gly Cys Thr Gly Ala Thr Gly
            325                 330                 335

Ala Ala Cys Gly Ala Ala Gly Ala Thr Ala Gly Cys Ala Thr Thr Cys
            340                 345                 350

Thr Gly Gly Cys Gly Gly Thr Gly Gly Cys Ala Ala Thr Ala
            355                 360                 365

Thr Thr Thr Thr Cys Ala Gly Cys Gly Cys Ala Thr Ala Cys Cys
            370                 375                 380

Cys Thr Gly Thr Ala Thr Cys Thr Gly Ala Thr Thr Gly Ala Ala Cys
385                 390                 395                 400

Gly Cys Ala Ala Ala Thr Ala Thr Ala Gly Cys Cys Gly Thr Gly
            405                 410                 415

Cys Gly Cys Gly Thr Gly Gly Ala Ala Gly Thr Gly Gly Thr Gly
            420                 425                 430

Cys Gly Cys Gly Cys Gly Gly Ala Ala Thr Thr Ala Thr Gly Cys
            435                 440                 445

Gly Cys Ala Gly Cys Cys Thr Gly Ala Gly Cys Thr Thr Thr Ala Gly
            450                 455                 460

Cys Ala Cys Cys Ala Ala Cys Cys Thr Gly Cys Ala Gly Ala Ala Ala
465                 470                 475                 480

Cys Gly Cys Gly Thr Gly Cys Gly Cys Gly Cys Ala Ala Ala Gly
            485                 490                 495

Ala Thr

<210> SEQ ID NO 3
<211> LENGTH: 498
<212> TYPE: PRT
<213> ORGANISM: Homo sapiens

<400> SEQUENCE: 3

Thr Gly Tyr Gly Ala Tyr Tyr Thr Asn Cys Cys Asn Cys Ala Arg Ala
1               5                   10                  15

Cys Asn Cys Ala Tyr Trp Ser Asn Tyr Thr Asn Gly Gly Asn Ala Ala
                20                  25                  30

Tyr Met Gly Asn Met Gly Asn Gly Cys Asn Tyr Thr Asn Ala Thr His
            35                  40                  45

Tyr Thr Asn Tyr Thr Asn Gly Gly Asn Cys Ala Arg Ala Thr Gly Gly
        50                  55                  60

Gly Asn Met Gly Asn Ala Thr His Trp Ser Asn Cys Cys Asn Thr Thr
65                  70                  75                  80

Tyr Trp Ser Asn Thr Gly Tyr Tyr Thr Asn Ala Ala Arg Gly Ala Tyr
                85                  90                  95

Met Gly Asn Cys Ala Tyr Gly Ala Tyr Thr Thr Tyr Met Gly Asn Ala
            100                 105                 110

Thr His Cys Cys Asn Cys Ala Arg Gly Ala Arg Gly Ala Arg Thr Thr
        115                 120                 125

Tyr Gly Ala Tyr Gly Gly Asn Ala Ala Tyr Cys Ala Arg Thr Thr Tyr
```

```
            130                 135                 140
Cys Ala Arg Ala Ala Arg Gly Cys Asn Cys Ala Arg Gly Cys Asn Ala
145                 150                 155                 160

Thr His Trp Ser Asn Gly Thr Asn Tyr Thr Asn Cys Ala Tyr Gly Ala
                165                 170                 175

Arg Ala Thr Gly Ala Thr Gly Cys Ala Arg Cys Ala Arg Ala Cys Asn
                180                 185                 190

Thr Thr Tyr Ala Ala Tyr Tyr Thr Asn Thr Thr Tyr Trp Ser Asn Ala
                195                 200                 205

Cys Asn Gly Ala Arg Ala Ala Tyr Trp Ser Asn Trp Ser Asn Gly Cys
                210                 215                 220

Asn Gly Cys Asn Thr Gly Gly Ala Arg Cys Ala Arg Ala Cys Asn
225                 230                 235                 240

Tyr Thr Asn Tyr Thr Asn Gly Ala Arg Ala Ala Arg Thr Thr Tyr Trp
                245                 250                 255

Ser Asn Ala Thr His Gly Ala Arg Tyr Thr Asn Thr Thr Tyr Cys Ala
                260                 265                 270

Arg Cys Ala Arg Ala Thr Gly Ala Ala Tyr Gly Ala Tyr Tyr Thr Asn
                275                 280                 285

Gly Ala Arg Gly Cys Asn Thr Gly Tyr Gly Thr Asn Ala Thr His Cys
                290                 295                 300

Ala Arg Gly Ala Arg Gly Thr Asn Gly Gly Asn Gly Thr Asn Gly Ala
305                 310                 315                 320

Arg Gly Ala Arg Ala Cys Asn Cys Cys Asn Tyr Thr Asn Ala Thr Gly
                325                 330                 335

Ala Ala Tyr Gly Ala Arg Gly Ala Tyr Trp Ser Asn Ala Thr His Tyr
                340                 345                 350

Thr Asn Gly Cys Asn Gly Thr Asn Met Gly Asn Ala Ala Arg Thr Ala
                355                 360                 365

Tyr Thr Thr Tyr Cys Ala Arg Met Gly Asn Ala Thr His Ala Cys Asn
                370                 375                 380

Tyr Thr Asn Thr Ala Tyr Tyr Thr Asn Ala Thr His Gly Ala Arg Met
385                 390                 395                 400

Gly Asn Ala Ala Arg Thr Ala Tyr Trp Ser Asn Cys Cys Asn Thr Gly
                405                 410                 415

Tyr Gly Cys Asn Thr Gly Gly Ala Arg Gly Thr Asn Gly Thr Asn
                420                 425                 430

Met Gly Asn Gly Cys Asn Gly Ala Arg Ala Thr His Ala Thr Gly Met
                435                 440                 445

Gly Asn Trp Ser Asn Tyr Thr Asn Trp Ser Asn Thr Thr Tyr Trp Ser
                450                 455                 460

Asn Ala Cys Asn Ala Ala Tyr Tyr Thr Asn Cys Ala Arg Ala Ala Arg
465                 470                 475                 480

Met Gly Asn Tyr Thr Asn Met Gly Asn Met Gly Asn Ala Ala Arg Gly
                485                 490                 495

Ala Tyr

<210> SEQ ID NO 4
<211> LENGTH: 166
<212> TYPE: PRT
<213> ORGANISM: Homo sapiens

<400> SEQUENCE: 4

Cys Asp Leu Pro Gln Thr His Ser Leu Gly Asn Arg Arg Ala Leu Ile
```

```
1               5                   10                  15
Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
            50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Ile Glu Arg Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 5
<211> LENGTH: 166
<212> TYPE: PRT
<213> ORGANISM: Homo sapiens

<400> SEQUENCE: 5

Cys Asn Leu Ser Gln Thr His Ser Leu Asn Asn Arg Arg Thr Leu Met
1               5                   10                  15

Leu Met Gly Gln Met Arg Arg Ile Ser Pro Phe Ser Cys Leu Lys Asp
            20                  25                  30

Arg His Asp Phe Glu Ile Pro Gln Glu Glu Phe Asp Gly Asn Gln Phe
            35                  40                  45

Gln Lys Ala Gln Ala Ile Ser Val Leu His Glu Met Met Gln Gln Thr
            50                  55                  60

Phe Asn Leu Phe Ser Thr Glu Asn Ser Ser Ala Ala Trp Glu Gln Thr
65                  70                  75                  80

Leu Leu Glu Lys Phe Ser Ile Glu Leu Phe Gln Gln Met Asn Asp Leu
            85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Met Glu Arg Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```